(12) United States Patent
Edwards et al.

(10) Patent No.: US 10,561,320 B2
(45) Date of Patent: Feb. 18, 2020

(54) TIME SYNCHRONIZATION IN A MEDICAL DEVICE SYSTEM OR NETWORK

(71) Applicant: ZOLL Medical Corporation, Chelmsford, MA (US)

(72) Inventors: Bruce Edwards, Marlborough, MA (US); Tim Stever, Lowell, MA (US); Suzanne Crowell, Beverly, MA (US); Gary A. Freeman, Waltham, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 60 days.

(21) Appl. No.: 15/387,119

(22) Filed: Dec. 21, 2016

(65) Prior Publication Data
US 2017/0231508 A1    Aug. 17, 2017

Related U.S. Application Data

(60) Provisional application No. 62/270,173, filed on Dec. 21, 2015.

(51) Int. Cl.
*A61B 5/0205* (2006.01)
*A61B 5/00* (2006.01)
(Continued)

(52) U.S. Cl.
CPC ........ *A61B 5/02055* (2013.01); *A61B 5/0022* (2013.01); *A61M 16/00* (2013.01);
(Continued)

(58) Field of Classification Search
CPC ... G06F 19/3418; A61B 5/0022; A61B 5/024; A61B 5/0004; A61B 5/0205;
(Continued)

(56) References Cited

U.S. PATENT DOCUMENTS 4,945,477 A    7/1990 Edwards
5,549,115 A    8/1996 Morgan et al.
(Continued)

OTHER PUBLICATIONS

Jiang Wu, et al., "Synchronizing Device Clocks Using IEEE 1588 and Blackfin Embedded Processors," Analog Dialogue 43-11, Nov. 2009, pp. 1-5 (5 pages).

Mike Jones, "Get in Sync! IEEE1588v2 Transparent Clock Benefits for Industrial Control Distributed Networks," Micrel Inc., San Jose, California, Mar. 22, 2012, pp. 1-13 (13 pages).

*Primary Examiner* — Deborah L Malamud

(74) *Attorney, Agent, or Firm* — Finch & Maloney PLLC

(57) ABSTRACT

Medical devices can perform a plurality of functions, such as sensing, monitoring, deriving and/or calculating various physiological statuses of a patient (e.g., blood pressure, temperature, respiration rate, etc.). Medical devices can also be used to image part or all of a patient's body, to deliver a treatment, or to manage information related to a patient's care. The present disclosure is directed at one or more devices that perform these functions using a plurality of processing circuits, wherein each processing circuit has a timing circuit with a local clock. These processing circuits can be connected via a network, and each timing circuit can communicate with at least one other timing circuit in order to detect and correct time-differences between their local clocks. In this way, multiple processing circuits can be synchronized with each other to facilitate diagnosis or treatment of a patient's condition, or other aspects of a patient's care.

31 Claims, 10 Drawing Sheets

(51) Int. Cl.
*A61N 1/39* (2006.01)
*A61M 16/00* (2006.01)
*A61B 5/0402* (2006.01)
*A61B 5/024* (2006.01)
*A61B 5/145* (2006.01)
*A61B 5/083* (2006.01)
*A61B 5/021* (2006.01)

(52) U.S. Cl.
CPC ............ *A61N 1/3925* (2013.01); *A61B 5/021* (2013.01); *A61B 5/024* (2013.01); *A61B 5/0402* (2013.01); *A61B 5/0836* (2013.01); *A61B 5/14542* (2013.01)

(58) Field of Classification Search
CPC ....... A61B 5/0402; A61B 5/11; A61B 5/0006; A61B 5/1118; A61B 5/7275; A61B 5/0245; A61B 5/0002; A61B 5/04012; A61B 5/05; H04L 67/12; H04L 67/22; H04L 7/0008; G06Q 50/24; A61N 1/37211; A61N 1/37282; G16H 50/20; Y04S 40/16
See application file for complete search history.

(56) References Cited

U.S. PATENT DOCUMENTS

| | | |
|---|---|---|
| 5,778,882 A | 7/1998 | Raymond et al. |
| 5,784,421 A | 7/1998 | Dolev et al. |
| 5,785,043 A | 7/1998 | Cyrus et al. |
| 5,860,918 A | 1/1999 | Schradi et al. |
| 5,891,046 A | 4/1999 | Cyrus et al. |
| 5,921,938 A | 7/1999 | Aoyama et al. |
| 5,951,485 A | 9/1999 | Cyrus et al. |
| 6,095,985 A | 8/2000 | Raymond et al. |
| 6,216,096 B1 | 4/2001 | Obermeier |
| 6,282,441 B1 | 8/2001 | Raymond et al. |
| 6,542,910 B2 | 4/2003 | Cork et al. |
| 7,124,190 B1 | 10/2006 | Moore |
| 7,774,052 B2 * | 8/2010 | Burton ................. A61B 5/0476 600/544 |
| 7,843,325 B2 * | 11/2010 | Otto ..................... A61B 5/0002 340/506 |
| 8,768,441 B2 | 7/2014 | De Zwart et al. |
| 2003/0065536 A1 | 4/2003 | Hansen et al. |
| 2004/0172070 A1 | 9/2004 | Moore et al. |

* cited by examiner

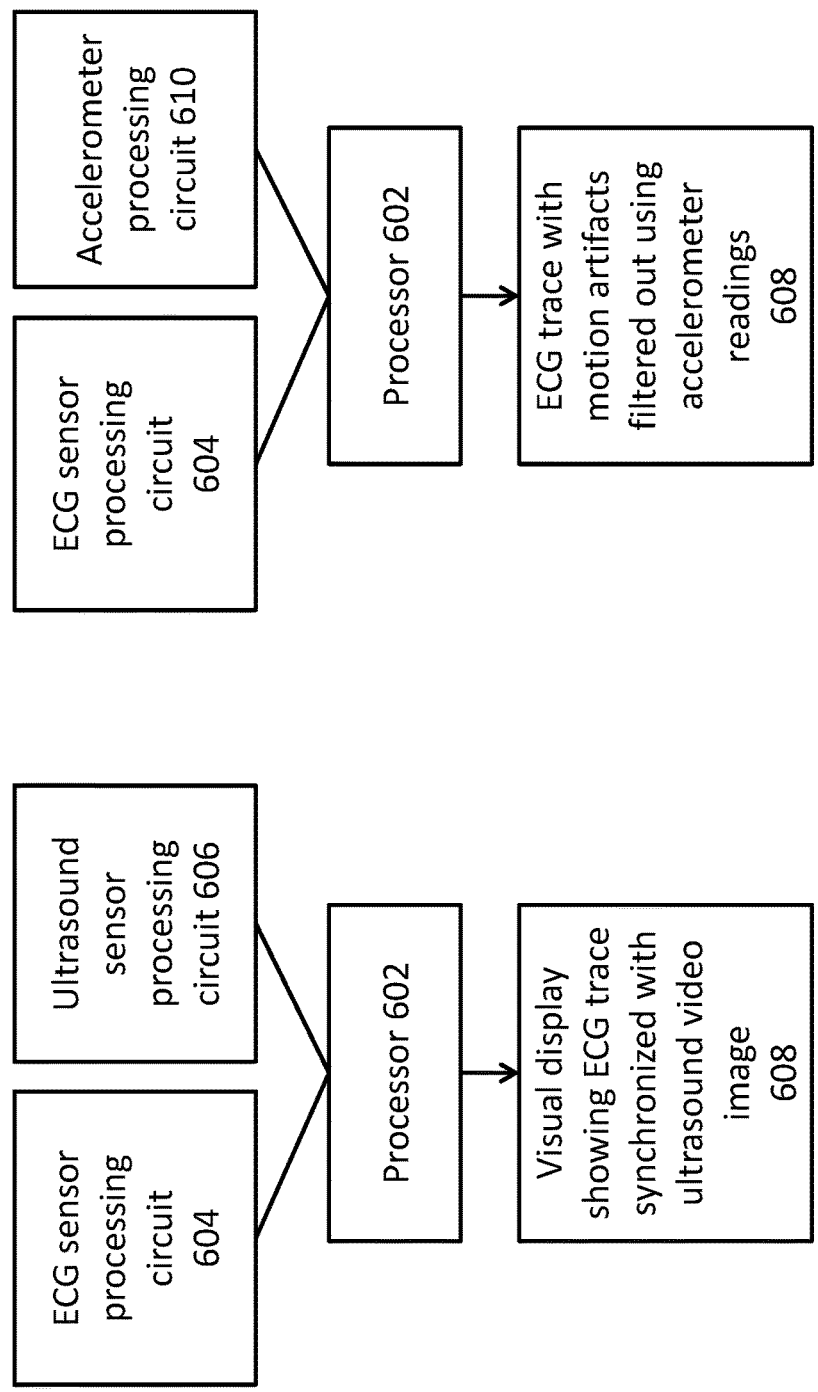

TIME SYNCHRONIZATION IN A MEDICAL DEVICE SYSTEM OR NETWORK

CROSS-REFERENCE TO RELATED APPLICATIONS

This application claims benefit of U.S. Provisional Patent Application No. 62/270,173, titled "Time Synchronization In A Medical Device System Or Network," filed Dec. 21, 2015, which is herein incorporated by reference in its entirety.

FIELD

Embodiments of the present disclosure relate generally to medical devices, and more particularly, to synchronization of functions within one or a plurality of medical devices.

BACKGROUND

Medical devices can perform a plurality of functions. For example, medical devices can be used to sense, monitor, derive and/or calculate any of a plurality of physiological statuses of a patient, including the patient's blood pressure, temperature, respiration rate, blood oxygen level, end-tidal carbon dioxide level, pulmonary function, blood glucose level, and/or weight. Medical devices can also be used to image or scan a patient's body, using any one of a number of methods, for instance, ultrasound, X-rays, computed tomography (CT), magnetic resonance imaging (MRI), molecular imaging, amongst others. Medical devices can also be used to deliver a treatment, such as facilitating or assisting a patient's breathing (e.g., using a ventilator), delivering an electric shock (e.g., using a defibrillator), delivering drugs, gases, compounds, or other medical agents, and other treatments. Furthermore, medical devices can also be used to assist in other aspects of a patient's care, such as reporting on the current real-time location of a patient, recording a patient's condition for later analysis, or communicating a patient's condition to a remote party, such as a hospital or physician.

In a medical treatment context, some or all of these functions can require tight time synchronization to function well, or at all. In particular, for applications where two or more functions need to be combined, synchronization between these two or more functions can be necessary or desirable.

SUMMARY

The techniques described herein provide for time synchronization of multiple processing circuits in a medical device system or network. For example, the system may account for communications latency that may be present between timing circuits of the system/network, resulting in a suitable shift between separate data streams for substantial synchronization of medical-related data produced by the processing circuits. In some cases, time differences between clocks of timing circuits may also be determined as part of the synchronization. In various embodiments, the medical device can be a portable medical treatment or monitoring device, such as a monitor (e.g., hospital, emergency services), defibrillator and/or Automatic External Defibrillator (AED). Alternatively, the medical system can comprise multiple medical devices, which can be used in cooperation with one another, for example, in close proximity to each other or geographically dispersed. The processing circuits being synchronized can be any apparatus or system for monitoring a physiological status of a patient, delivering or facilitating a treatment for the patient, or recording or updating information related to the patient, the apparatus, or the system itself.

In some embodiments, the medical system involves the time synchronization of multiple medical devices that form a dynamically secure communications network. Such a secure network may be reconfigurable in a simple manner (e.g., automatically, manually) such that devices may seamlessly join or leave the secure network, triggered by simple actions (e.g., user actuation, NFC activation, radio frequency, proximity detection, etc.). The medical device(s) may be provided as part of a single integrated apparatus (e.g., circuits within a housing performing various tasks involving sensing, communications, data transfer, processing, analysis, etc.), as separate apparatuses having various medical-related functions, and/or combinations thereof. That is, multiple apparatuses each with one or more processing circuits associated therewith may form a dynamically secure reconfigurable network where, upon entering the network, using processes described herein, each of the processing circuits may be substantially synchronized with one another. This synchronization may account for a number of possible sources of time discrepancy, such as differences in time stamping, communications latency during signal transmittance and/or other sources.

According to Example 1, certain embodiments of the present disclosure are directed at a medical system comprising: a plurality of processing circuits in communication with one another, each processing circuit configured to provide medical-related data; a plurality of timing circuits, each timing circuit having a clock, wherein at least some of the timing circuits are each associated with a different processing circuit of the plurality of processing circuits, and wherein each timing circuit is configured to communicate with at least one other timing circuit and produce at least one time stamped signal for the respective timing circuit and determine a communication latency between timing circuits; and a processor configured to analyze the communication latency between timing circuits and adjust time-alignment of medical-related data from at least some of the plurality of processing circuits so as to substantially synchronize the medical-related data provided from the at least some of the plurality of processing circuits.

According to Example 2, certain embodiments of the present disclosure are directed at Example 1, wherein the processor is configured to determine time differences between the clocks of the timing circuits during communication of the processing circuits, and correct for the time differences between the clocks.

According to Example 3, certain embodiments of the present disclosure are directed at any of Examples 1-2, wherein each timing circuit is further configured to correct for a time difference between the clock of the timing circuit and another timing circuit.

According to Example 4, certain embodiments of the present disclosure are directed at Example 1-3, wherein the plurality of processing circuits include at least one sensor configured to monitor a physiological status of a patient and to generate a set of sensor data based on the physiological status.

According to Example 5, certain embodiments of the present disclosure are directed at any of Examples 1-4, wherein the at least one sensor includes an electrocardiogram (ECG) sensor configured to generate one or more ECG waveforms.

According to Example 6, certain embodiments of the present disclosure are directed at any of Examples 1-5, wherein the at least one sensor further includes a second sensor comprising at least one of a heartbeat sensor configured to monitor a heartbeat of the patient, a blood oxygen sensor configured to monitor a blood oxygen level of the patient, a carbon dioxide sensor configured to monitor an end-tidal carbon dioxide level of the patient, and an ultrasound sensor configured to generate an ultrasound image of the patient; and a timing circuit associated with the second sensor is configured to be substantially synchronized with a timing circuit associated with the ECG sensor.

According to Example 7, certain embodiments of the present disclosure are directed at any of Examples 1-6, wherein the at least one sensor includes a blood pressure sensor configured to monitor a blood pressure of the patient and a heartbeat monitor configured to monitor a heartbeat of the patient; a timing circuit associated with the blood pressure sensor is configured to be substantially synchronized with a timing circuit associated with the heartbeat monitor; and wherein the blood pressure sensor is configured to record a systolic blood pressure measurement when the heartbeat monitor indicates that the patient's heart is beating.

According to Example 8, certain embodiments of the present disclosure are directed at any of Examples 1-7, wherein the at least one sensor includes an accelerometer configured to monitor an acceleration associated with the patient and to generate a set of sensor data based on the acceleration; and the processor is configured to modify at least one other set of sensor data to compensate for inaccuracies associated with the acceleration.

According to Example 9, certain embodiments of the present disclosure are directed at any of Examples 1-8, wherein the at least one sensor includes at least one of a blood pressure sensor, a heartbeat sensor, a blood oxygen sensor, a carbon dioxide sensor, an ultrasound sensor, an accelerometer, an electrocardiogram (ECG) sensor, a spectral muscle-chemistry sensor, a temperature sensor, a videocamera, and a microphone.

According to Example 10, certain embodiments of the present disclosure are directed at any of Examples 1-9, wherein each timing circuit is configured to communicate with at least one other timing circuit via a wired or optical serial communications network.

According to Example 11, certain embodiments of the present disclosure are directed at any of Examples 1-10, wherein each timing circuit is configured to communicate with at least one other timing circuit via a wireless network.

According to Example 12, certain embodiments of the present disclosure are directed at any of Examples 1-11, wherein the plurality of processing circuits, the plurality of timing circuits, and the processor are integrated into a single device.

According to Example 13, certain embodiments of the present disclosure are directed at any of Examples 1-12, wherein at least two of the plurality of processing circuits, and at least two of the plurality of timing circuits, are integrated into a single device; and wherein at least some of the plurality of processing circuits and at least some of the plurality of timing circuits are integrated into devices other than the single device.

According to Example 14, certain embodiments of the present disclosure are directed at any of Examples 1-13, wherein the plurality of processing circuits, the plurality of timing circuits, and the processor are dispersed across two or more devices connected via a network.

According to Example 15, certain embodiments of the present disclosure are directed at any of Examples 1-14, wherein a processing circuit of the plurality of processing circuits is configured to be dynamically connected to and disconnected from the processor, and wherein the processing circuit is configured to communicate with the processor only when the processing circuit is dynamically connected.

According to Example 16, certain embodiments of the present disclosure are directed at any of Examples 1-15, wherein the plurality of processing circuits include at least one treatment circuit configured to administer a treatment to the patient.

According to Example 17, certain embodiments of the present disclosure are directed at any of Examples 1-16, wherein the treatment circuit includes at least one of a ventilator and a defibrillator shock device.

According to Example 18, certain embodiments of the present disclosure are directed at any of Examples 1-17, wherein each timing circuit of at least some of the plurality of timing circuits is configured to: receive a synchronization message having a time stamp from another timing circuit acting as a master timing circuit; send a delay request message at a delay request sending time; determine a master-slave time difference based on at least the time stamp and the delay request sending time; and adjust the clock of the timing circuit based on the master-slave time difference.

According to Example 19, certain embodiments of the present disclosure are directed at any of Examples 1-18, wherein each timing circuit is configured to: determine whether to act as a master timing circuit or a slave timing circuit; when acting as a slave timing circuit, to: receive a synchronization message having a time stamp from another timing circuit acting as a master timing circuit, send a delay request message at a delay request sending time, determine a master-slave time difference based on at least the time stamp and the delay request sending time, and adjust the clock of the timing circuit based on the master-slave time difference; and when acting as a master timing circuit, to: send the synchronization message having the time stamp, and receive the delay request message from another timing circuit acting as a slave timing circuit.

According to Example 20, certain embodiments of the present disclosure are directed at any of Examples 1-19, wherein at least some of the timing circuits are configured to determine whether to act as a master timing circuit or a slave timing circuit based on a pre-defined setting.

According to Example 21, certain embodiments of the present disclosure are directed at any of Examples 1-20, wherein each timing circuit of at least some of the timing circuits is configured to determine whether to act as a master timing circuit or a slave timing circuit based on communications with at least one other timing circuit.

According to Example 22, certain embodiments of the present disclosure are directed at any of Examples 1-21, wherein each of the plurality of timing circuits is further configured to: when acting as a master timing circuit: send a delay response message in response to the delay request message; and when acting as a slave timing circuit: receive the delay response message at a delay response receipt time from the other timing circuit acting as the master timing circuit, and determine the master-slave time difference based on at least the delay response receipt time.

According to Example 23, certain embodiments of the present disclosure are directed at any of Examples 1-22, wherein the plurality of processing circuits are configured to form a secure communications network.

According to Example 24, certain embodiments of the present disclosure are directed at any of Examples 1-23, wherein the plurality of processing circuits are each configured to dynamically join or leave the secure communications network.

According to Example 25, certain embodiments of the present disclosure are directed at any of Examples 1-24, wherein the medical system is configured to output an indication representative of the communication latency between timing circuits to a medium for user review.

According to Example 26, certain embodiments of the present disclosure are directed at a method of synchronizing a medical system, the method comprising: providing, from each of a plurality of processing circuits, a set of medical-related data; providing a plurality of timing circuits, each timing circuit having a clock, wherein at least some of the timing circuits are each associated with a different processing circuit of the plurality of processing circuits; at each timing circuit: communicating with at least one other timing circuit, and determining a time difference between the clocks of the timing circuit and the at least one other timing circuit; and synchronizing, at a processor, medical-related data generated from the plurality of processing circuits.

According to Example 27, certain embodiments of the present disclosure are directed at Examples 26, the method further comprising at each of at least some of the plurality of timing circuits, correcting for the determined time difference.

According to Example 28, certain embodiments of the present disclosure are directed at any of Examples 26,-27 wherein the plurality of processing circuits includes at least one sensor configured to monitor a physiological status of a patient and to generate a set of sensor data based on the physiological status.

According to Example 29, certain embodiments of the present disclosure are directed at any of Examples 26-28, wherein the at least one sensor includes an electrocardiogram (ECG) sensor configured to generate one or more ECG waveforms.

According to Example 30, certain embodiments of the present disclosure are directed at any of Examples 26-29, wherein the at least one sensor further includes a second sensor drawn from at least one of a heartbeat sensor configured to monitor a heartbeat of the patient, a blood oxygen sensor configured to monitor a blood oxygen level of the patient, a carbon dioxide sensor configured to monitor an end-tidal carbon dioxide level of the patient, and an ultrasound sensor configured to generate an ultrasound image of the patient; the method further comprising determining and correcting for a time difference between a timing circuit associated with the ECG sensor and a timing circuit associated with the second sensor.

According to Example 31, certain embodiments of the present disclosure are directed at any of Examples 26-30, wherein the at least one sensor includes a blood pressure sensor configured to monitor a blood pressure of the patient and a heartbeat monitor configured to monitor a heartbeat of the patient; the method further comprising: determining and correcting for a time difference between a timing circuit associated with the blood pressure sensor and a timing circuit associated with the heartbeat monitor; and taking a systolic blood pressure measurement using the blood pressure sensor when the heartbeat monitor indicates that the patient's heart is beating.

According to Example 32, certain embodiments of the present disclosure are directed at any of Examples 26-31, wherein the at least one sensor includes an accelerometer configured to monitor an acceleration associated with the patient and to generate a set of sensor data based on the acceleration; and the method further comprises modifying, at the processor, at least one other set of sensor data to compensate for inaccuracies associated with the acceleration.

According to Example 33, certain embodiments of the present disclosure are directed at any of Examples 26-32, wherein the at least one sensor includes at least one of a blood pressure sensor, a heartbeat sensor, a blood oxygen sensor, a carbon dioxide sensor, an ultrasound sensor, an accelerometer, an electrocardiogram (ECG) sensor, a spectral muscle-chemistry sensor, a temperature sensor, a video-camera, and a microphone.

According to Example 34, certain embodiments of the present disclosure are directed at any of Examples 26-33, wherein the communicating with at least one other timing circuit is accomplished via a wired or optical serial communications network.

According to Example 35, certain embodiments of the present disclosure are directed at any of Examples 26-34, wherein the communicating with at least one other timing circuit is accomplished via a wireless network.

According to Example 36, certain embodiments of the present disclosure are directed at any of Examples 26-35, wherein the plurality of processing circuits, the plurality of timing circuits, and the processor are integrated into a single device.

According to Example 37, certain embodiments of the present disclosure are directed at any of Examples 26-36, wherein at least two of the plurality of processing circuits, and at least two of the plurality of timing circuits, are integrated into a single device; and wherein at least some of the plurality of processing circuits and at least some of the plurality of timing circuits are integrated into devices other than the single device.

According to Example 38, certain embodiments of the present disclosure are directed at any of Examples 26-37, wherein the plurality of processing circuits, the plurality of timing circuits, and the processor are dispersed across two or more devices connected via a network.

According to Example 39, certain embodiments of the present disclosure are directed at any of Examples 26-38, wherein a processing circuit of the plurality of processing circuits is configured to be dynamically connected to and disconnected from the processor, and wherein the processing circuit is configured to communicate with the processor only when the processing circuit is dynamically connected.

According to Example 40, certain embodiments of the present disclosure are directed at any of Examples 26-39, wherein at least one of the timing circuits is associated with a treatment circuit configured to administer a treatment to the patient.

According to Example 41, certain embodiments of the present disclosure are directed at any of Examples 26-40, wherein the treatment circuit includes at least one of a ventilator and a defibrillator shock device.

According to Example 42, certain embodiments of the present disclosure are directed at any of Examples 26-41, further comprising: at each timing circuit of at least some of the timing circuits: receiving a synchronization message having a time stamp from another timing circuit acting as a master timing circuit; sending a delay request message at a delay request sending time; determining a master-slave time difference based on at least the time stamp and the delay request sending time; and adjusting the clock of the timing circuit based on the master-slave time difference.

According to Example 43, certain embodiments of the present disclosure are directed at any of Examples 26-42, further comprising: at each timing circuit: determining whether to act as a master timing circuit or a slave timing circuit; when acting as a slave timing circuit: receiving a synchronization message having a time stamp from another timing circuit acting as a master timing circuit, sending a delay request message at a delay request sending time, determining a master-slave time difference based on at least the time stamp and the delay request sending time, and adjusting the clock of the timing circuit based on the master-slave time difference; and when acting as a master timing circuit: sending the synchronization message having the time stamp, and receiving the delay request message from another timing circuit acting as a slave timing circuit.

According to Example 44, certain embodiments of the present disclosure are directed at any of Examples 26-43, wherein at at least some of the timing circuits, the determining whether to act as a master timing circuit or a slave timing circuit is based on a pre-defined setting.

According to Example 45, certain embodiments of the present disclosure are directed at any of Examples 26-44, wherein at at least some of the timing circuits, the determining whether to act as a master timing circuit or a slave timing circuit includes communicating with at least one other timing circuit.

According to Example 46, certain embodiments of the present disclosure are directed at any of Examples 26-45, further comprising: at each timing circuit: when acting as a master timing circuit: sending a delay response message in response to the delay request message; and when acting as a slave timing circuit: receiving the delay response message at a delay response receipt time from the other timing circuit acting as the master timing circuit; wherein the determination of the master-slave time difference is also based on the delay response receipt time.

According to Example 47, certain embodiments of the present disclosure are directed at any of Examples 26-46, further comprising forming a secure communications network between the plurality of processing circuits.

According to Example 48, certain embodiments of the present disclosure are directed at any of Examples 26-47, wherein the plurality of processing circuits are each configured to dynamically join or leave the secure communications network.

According to Example 49, certain embodiments of the present disclosure are directed at any of Examples 26-48, further comprising outputting an indication representative of the communication latency between timing circuits to a medium for user review.

These and other capabilities of the disclosed subject matter will be more fully understood after a review of the following figures, detailed description, and claims. It is to be understood that the phraseology and terminology employed herein are for the purpose of description and should not be regarded as limiting.

BRIEF DESCRIPTION OF THE DRAWINGS

For a more complete understanding of the present disclosure, reference is now made to the following descriptions taken in conjunction with the accompanying drawing, in which:

FIG. 6A illustrates how an ECG sensor circuit can be synchronized and combined with an ultrasound sensor circuit, according to some embodiments.

FIG. 6B illustrates how an ECG sensor circuit can be synchronized and combined with an accelerometer circuit, according to some embodiments.

DETAILED DESCRIPTION

Figure 1:
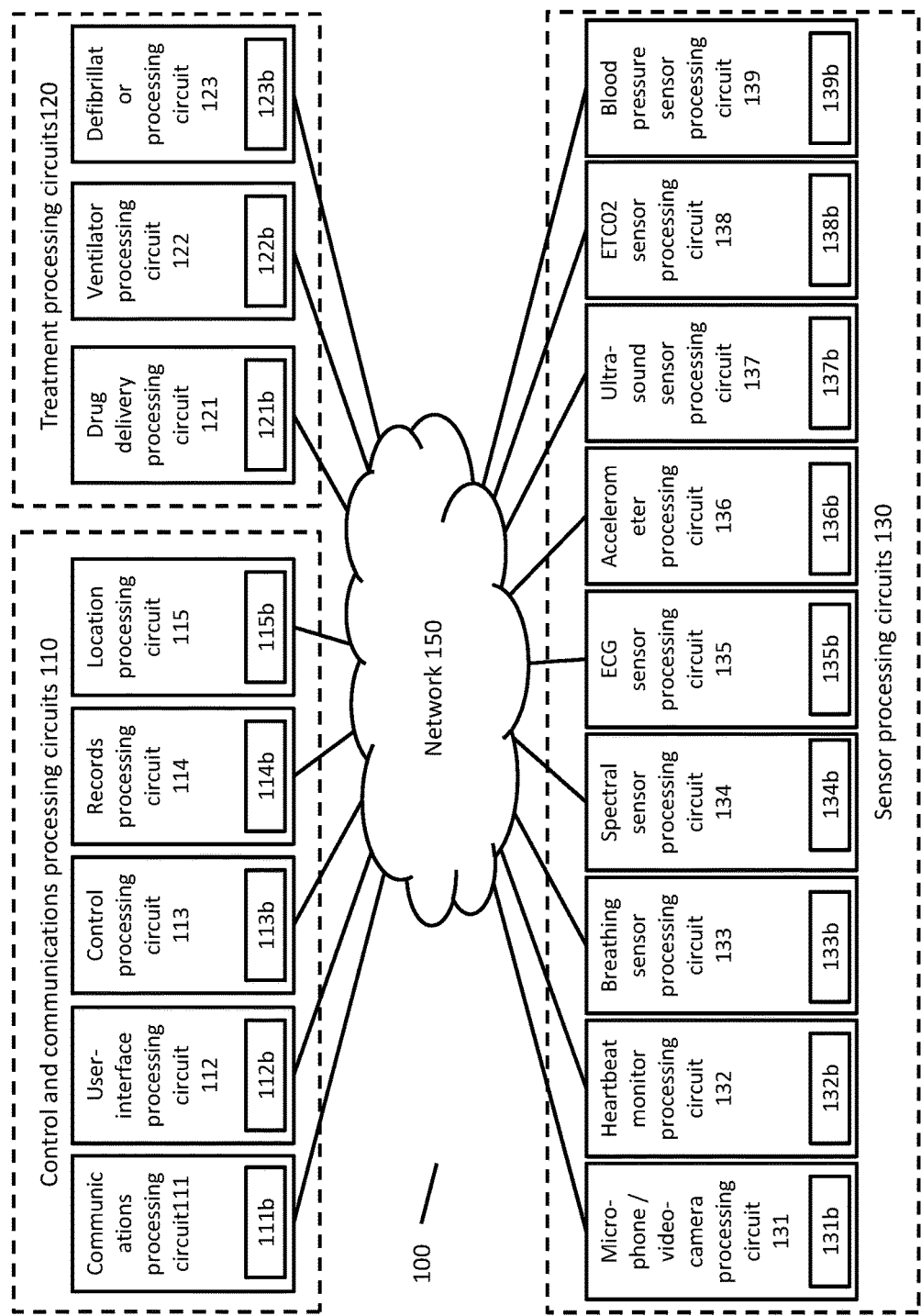
FIG. 1 depicts an exemplary medical system, according to some embodiments.

As discussed above, medical devices can perform a plurality of functions. These functions can include sensing, monitoring, deriving and/or calculating any of a plurality of physiological statuses of a patient. Medical devices can also be used to image or scan a patient's body, to deliver a treatment, or to assist in other aspects of a patient's care. In some cases, it can be desirable to time-synchronize two or more of these functions. For example, it can be desirable to synchronize two different sensors monitoring two different physiological statuses of a patient. It can also be desirable to synchronize a sensor monitoring a physiological status of a patient with a patient data record, or with a treatment device delivering a treatment.

The present disclosure is directed at methods, systems and apparatus for providing time-synchronization across multiple processing circuits in a medical device system or network. According to some embodiments, each processing circuit can be provided with a timing circuit with a local clock. The timing circuits can each include a local clock, and the timing circuits can communicate with one another to determine and correct for variations between the local clocks of the timing circuits. In some embodiments, one of the timing circuits can act as a "master" timing circuit, and each of the other timing circuits can act as "slave" timing circuits that synchronize with the local clock at the master timing circuit. In some cases, these timing circuits can enable the processing circuits of medical system to achieve sub-microsecond level synchronization. In other cases, these timing circuits can enable the processing circuits to achieve synchronization within the range of 1-100 microseconds (e.g., 1-10 microseconds), or less. Specific embodiments for addressing the aforementioned needs, as well as other needs, are described in further detail below.

In some embodiments, the present disclosure is directed at synchronizing multiple processing circuits in a single medical device. For example, the medical device can be a defibrillator, an Automatic External Defibrillator (AED) and/or a patient monitoring device that monitors one or more physiological statuses of a patient. The disclosed methods, systems and apparatus can be used to synchronize the operations of two or more of these processing circuits.

In other embodiments, the present disclosure is directed at synchronizing processing circuits dispersed across two or more medical devices in close proximity to one another, e.g., within the same ambulance or within the same room. The disclosed methods, systems and apparatus can be used to synchronize the operations of these two medical devices over a local wired or wireless network.

In yet other embodiments, the present disclosure is directed at synchronizing processing circuits dispersed across two or more medical devices that are geographically distant from one another. For instance, one medical device can be situated in an ambulance, whereas another medical device can be situated in a hospital or other medical care facility. As another example, one medical device can be situated in an ambulance or medical care facility, and another medical device can be situated at a remote patient records facility or patient analysis facility. The disclosed methods, systems and apparatus can be used to synchronize the operations of these medical devices over a long-distance wired or wireless network.

In some embodiments, the present disclosure relates to the time synchronization of processing circuits that form a dynamically secure reconfigurable communications network. As noted above, the processing circuits may be provided as part of a single integrated medical apparatus and/or provided within separate medical apparatuses. In accordance with aspects of the present disclosure, once the processing circuit(s) join the secure network, the processing circuits may be substantially synchronized with one another.

FIG. 1 depicts an exemplary medical system 100, according to some embodiments. The medical system 100 can include a plurality of processing circuits, including control and communications processing circuits 110, treatment processing circuits 120, and/or sensor processing circuits 130. Each processing circuit can be configured to perform different tasks of a plurality of tasks, and can also be configured to output a set of data, such as a continuous or discrete data stream.

Control and communications processing circuits 110 can include, without limitation, communications processing circuit 111, user-interface processing circuit 112, control processing circuit 113, records processing circuit 114, and/or location processing circuit 115. Communications processing circuit 111 can be configured to facilitate communications between the medical system 100 and an outside device or system (not shown), or to facilitate communications between processing circuits within medical system 100. For example, communications processing circuit 111 can comprise a wireless transceiver configured to communicate with an external network using cellular technologies such as 3GPP, or communications processing circuit can function as a gateway or load balancer managing internal communications between processing circuits within medical system 100. Communications processing circuit can also include short-range wireless transceivers, such as Bluetooth or WiFi, configured to communicate with an outside device or system (not shown) or to facilitate communications within medical system 100. Communications processing circuit can also comprise wired communications interfaces, such as Ethernet, intranet, RS232, USB, or other types of ports or interfaces.

User interface processing circuit 112 can be configured to operate a user interface for receiving user input and for displaying data, results or analyses to a user. User interface processing circuit 112 can comprise any known user interface in the art, including without limitation, a touchscreen, keyboard, mouse, trackball, a monitor or display, speakers, and/or haptic feedback mechanisms. Control processing circuit 113 can be configured to control and/or coordinate the functions of other processing circuits, and can comprise any special-purpose or general purpose processor. Records processing circuit 114 can be configured to record and/or keep track of a patient's medical record, including recording and updating a patient's condition in real-time, accessing a patient's past medical records, and keeping track of notes from physicians and other healthcare providers. Records processing circuit 114 can also comprise any special-purpose or general-purpose processor or microprocessor, and/or any associated volatile or non-volatile memory. Location processing circuit 115 can be configured to handle location-related tasks associated with the patient. For example, location circuit 115 can comprise a GPS receiver configured to determine a location of interest, such as a patient's current location or a care-giver's current location. Location processing circuit 115 can also hardware, and/or be configured to execute software, configured to determine an optimal route between two points, and to provide directions to a user regarding how to navigate to an appropriate location. Location processing circuit 115 can also be configured to determine the closest available point of interest, such as the closest available healthcare facility.

Treatment processing circuits 120 can include, without limitation, a drug delivery processing circuit 121, a ventilator processing circuit 122, and/or a defibrillator processing circuit 123. Drug delivery processing circuit 121 can be any processing circuit configured to administer a drug, compound, or other medical agent to a patient. The drug, compound, or other medical agent can be delivered in a liquid form, a gaseous form, a tablet form, or some other form. Ventilator processing circuit 122 can be any processing circuit configured to facilitate or assist a patient's breathing. Defibrillator processing circuit 123 can be any processing circuit configured to deliver a therapeutic electric shock to, for example, re-start or stabilize a patient's heart rhythm.

Sensor processing circuits 130 can include, without limitation, microphone/video camera processing circuit 131, heartbeat monitor processing circuit 132, breathing sensor processing circuit 133, spectral muscle-chemistry sensor processing circuit 134, ECG sensor processing circuit 135, accelerometer processing circuit 136, ultrasound sensor processing circuit 137, end-tidal carbon dioxide (ETCO2) sensor processing circuit 138, and/or blood pressure sensor processing circuit 139. Microphone/video camera circuit 131 can be any processing circuit configured to monitor a patient's physiological condition using a microphone, video camera, or photo camera. Heartbeat monitor 132 can be any processing circuit configured to monitor and measure a patient's heartbeat, using for instance, haptic or auditory sensors. Breathing sensor processing circuit 133 can be any processing circuit configured to monitor a patient's respiratory rate, or other aspects related to a patient's breathing. Spectral muscle-chemistry sensor processing circuit 134 can be any processing circuit configured to use reflectance spectroscopy as a method to diagnose or determine a patient's condition. ECG sensor processing circuit 135 can be any processing circuit configured to measure, monitor, and/or calculate a patient's electrocardiogram (ECG) waveform.

Accelerometer processing circuit 136 can be any processing circuit configured to measure an acceleration associated with a patient. For example, accelerometer processing circuit 136 can comprise an accelerometer unit embedded into or integrated into a device positioned close to a patient, or within a vehicle transporting the patient; by measuring the acceleration associated with the device and/or the vehicle, the accelerometer can estimate the patient's acceleration by assuming that the patient is also being subjected to the same acceleration forces. Accelerometer processing circuit 136 can also comprise a wired or wireless sensor configured to be attached to a patient, and to measure the patient's motion or acceleration (e.g., to detect a patient's shivering, or ambulatory motions). Ultrasound sensor processing circuit 137 can comprise a processing circuit configured to generate an ultrasound image of all or a portion of a patient's body. ETCO2 sensor processing circuit 138 can comprise any processing circuit configured to measure, monitor, or derive by calculation a patient's end-tidal carbon dioxide level. Blood pressure sensor circuit 139 can comprise any processing circuit configured to measure a patient's blood pressure.

While FIG. 1 lists a plurality of processing circuit types, many other types of processing circuits are also possible. For example, the medical system 100 can also comprise processing circuits associated with a blood-oxygen level sensor, a pulse oximetry sensor, a reflectance monitoring sensor, an X-ray, MRI, or CT scanner, a blood glucose sensor, and/or a temperature sensor. Each of the aforementioned processing circuits can include any or all of a sensing or implementing instrument (e.g., the leads for an ECG monitor, or a pressure sensor for a blood pressure sensor), any devices, systems, or software necessary to power, operate, and/or control said sensing/implementing instrument, as well as any devices, systems, or software necessary to interpret, analyze, record, or track readings or signals from said sensing/implementing instruments. For example, each processing circuit can include any or all of a general-purpose, programmable processor or microprocessor, a special-purpose processor or microprocessor, an application-specific integrated circuit (ASIC), volatile and/or non-volatile memory, shift registers, data buses, serial-to-parallel converters, analog-to-digital converters, multiplexers and/or demultiplexers, amplifiers, and/or filters. Each of the aforementioned processing circuits can also implement software stored in memory and/or executed on a single or on shared processors. In some embodiments, each of the aforementioned circuits can be implemented as separate processors running software stored in memory.

Implementing some or all of the above-mentioned processing circuits as separate standalone hardware devices, or as separate processors, can be advantageous in certain circumstances. For example, it can sometimes be desirable to separate processing circuits and/or multiple processors for power distribution, shared memory and/or power sensitivity reasons, such as to relieve computational burdens associated with medical applications (e.g., patient monitoring, providing feedback/instructions to caregivers, providing secure exchange of substantial amounts of data, etc.). As one illustrative example, defibrillator processing circuit 123 can be configured to activate or direct large doses of electrical voltage or current. Leakage currents or induced electromagnetic radiation from these large doses of electrical voltage or current can be harmful to the operation of other, more sensitive processing circuits (e.g., ECG sensor circuit 135). Or as another example, certain more critical processing circuits, such as ventilator processing circuit 122, can be run off of a dedicated power supply separate from other processing circuits to mitigate the risk of power supply interruptions disrupting operations.

It can also be desirable to separate processing circuits for security reasons. For instance, communications processing circuit 111, records processing circuits 114, and/or user-interface processing circuit 112 can be subject to strict security protocols that mitigate the risk of unauthorized copying, eavesdropping, or tampering of patient data. However, such security protocols may be unnecessary for other processing circuits, such as accelerometer processing circuit 136 or blood pressure sensor processing circuit 139, and can unnecessarily slow or hamper the operations of these other processing circuits. As a result, separating the functions of a medical system into discrete processing circuits, wherein some circuits incorporate added security protocols, can allow the medical system to perform its functions faster and more efficiently.

As another example, it can be desirable to separate processing circuits for reasons related to computational efficiency and cost. Certain types of processing circuits can be uniquely suited for certain types of tasks, while being relatively inefficient at other types of tasks. Since the above-mentioned processing circuits can be configured to perform a wide variety of tasks, the processor, software, and/or hardware of each processing circuit can be tailored to best suit the type of task it is responsible for. For instance, ECG sensor processing circuit or ultrasound sensor processing circuit can require advanced graphics or digital signal processing capabilities, whereas records processing circuit may require advanced database access capabilities. Certain processing circuits may require high performing hardware, whereas others may require only relatively inexpensive hardware. As a result, using a processing circuit, such as a single processor, that multitasks across all the different functions performed by each of the processing circuits can be inefficient and unduly expensive.

As another example, it can also be desirable to separate processing circuits for portability reasons, or to enable operation over large, dispersed geographic areas. Embodiments illustrating such configurations are described in further detail below in relation to FIG. 2.

FIG. 1 is exemplary only, and may be modified by adding or subtracting processing circuits, as well as by integrating processing circuits into larger, more general circuits, and/or dividing processing circuits into finer subcomponents.

Each of the aforementioned processing circuits can be connected to at least one, and possibly all, other processing circuits via a network 150. The network 150 can be a wired or wireless network, and can include, without limitation, an Ethernet network, a cellular network, a Bluetooth network, and/or other types of networks. The network 150 can link processing circuits integrated into a single portable medical device, such as a defibrillator, Automatic External Defibrillator (AED), wearable defibrillator, patient medical sign monitoring tool, or other device. The network 150 can also link processing circuits dispersed in multiple medical devices within close proximity to one another, as well as multiple medical devices and systems located far apart from one another (e.g., in another city, country, or continent). While FIG. 1 depicts each processing circuit as being connected to the network 150 in a hub-and-spoke architecture, other network topologies are also possible. Examples of other possible network topologies are discussed below in relation to FIGS. 5A and 5B.

Each of the aforementioned processing circuits can also include or be associated with a timing circuit. For example, communications circuit 111 can include a timing circuit 111$b$, user-interface circuit 112 can include a timing circuit 112$b$, etc. as shown in FIG. 1 for each circuit. Each of the timing circuits can be associated with a processing circuit, and can be configured to communicate with at least some of the other timing circuits, via network 150, in order to coordinate timing among the processing circuits. Timing circuits can comprise any of the components that may make up a processing circuit, as described above. In some instances, timing circuits can also share components (e.g., processors or system resources such as memory) with the processing circuit it is associated with. In some embodiments, timing circuits can also include software that is stored in memory, wherein the software is executed by either the processing circuit with which the timing circuit is associated, or by a separate processing circuit. As discussed above, the timing circuits can each include a local clock, and the timing circuits can communicate with one another to determine and correct for variations between the local clocks of the timing circuits. In some embodiments, one of the timing circuits can act as a "master" timing circuit, and each of the other timing circuits can act as "slave" timing circuits that synchronize with the local clock at the master timing circuit. In some cases, these timing circuits can enable the processing circuits of medical system 100 to achieve sub-microsecond level synchronization. The operation of the timing circuits are described in greater detail below.

Figure 2:
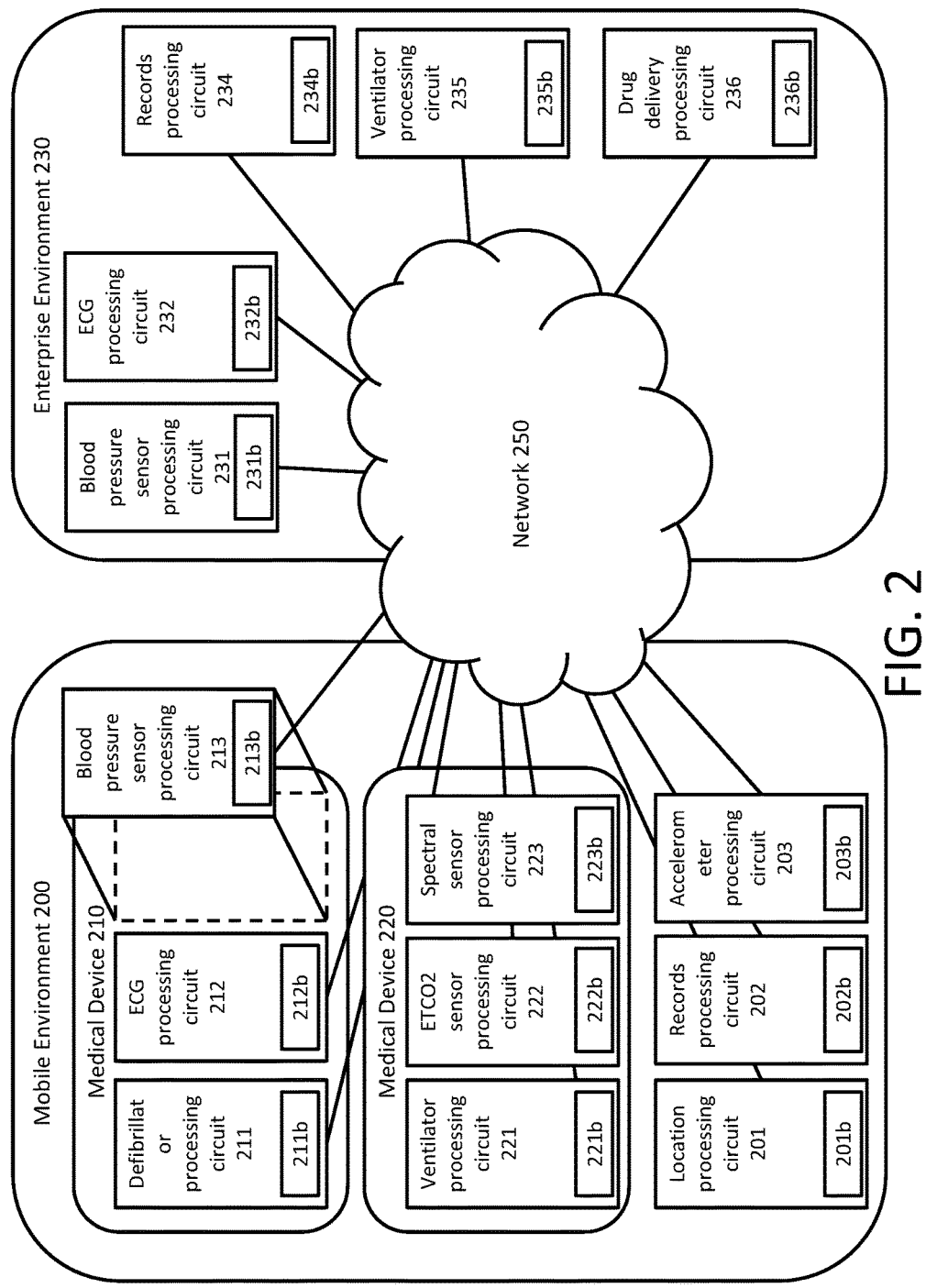
FIG. 2 depicts one potential embodiment of a medical system, according to some embodiments.

FIG. 2 depicts one potential embodiment of medical system 100. FIG. 2 includes a mobile environment 200, which can be a mobile clinic, an ambulance, or other type of mobile healthcare vehicle or facility. FIG. 2 also includes an enterprise environment 230, which can be a hospital, clinic, healthcare processing center, and/or other environment with a fixed location. Mobile environment 200 can include a first medical device 210 as well as a second medical device 220, each of which can serve different purposes and can include different processing circuits. For example, the first medical device 210 can be a defibrillator or Automated External Defibrillator (AED) that comprises a defibrillator processing circuit 211, an ECG processing circuit 212, and a blood pressure sensor processing circuit 213. The second medical device 220 can be a patient vital-sign monitoring device that can comprise a ventilator processing circuit 221, an ETCO2 sensor processing circuit 222, and a spectral muscle-chemistry sensor processing circuit 223. The mobile environment can also include integrated circuits, such as location processing circuit 201, records processing circuit 202 and accelerometer processing circuit 203. For example, these processing circuits can be integrated into or deployed in an ambulance to assist an ambulance driver in the front and/or EMS technician in the back to navigate the ambulance; locate the nearest healthcare facility; access, edit, and/or update a patient's medical record; and determine a motion or acceleration associated with the ambulance.

In some embodiments, some or all of these processing circuits can be detached or detachably coupled with the device or system with which it is associated. For example, blood pressure sensor circuit 213 is shown as being detached or detachably coupled with medical device 210. As used herein, a processing circuit can be considered "detachably coupled" with a device if it is configured to be physically coupled to the device using a removable or detachable connection, such as a removable wire, plug, adapter, or bus connection. A processing circuit can be considered "detached" from, yet "associated" with a device, if it is configured to initiate a wireless connection with the device, either automatically under certain conditions (e.g., when the processing circuit is within range of the device, or when one of the device and/or the processing circuit is turned on), or when instructed to by a user. In such embodiments, one processing circuit can be used with multiple medical devices and/or systems, and one medical device and/or system can be configured to operate with many different types of processing circuits. Processing circuits can be configured to "pair" with a particular medical device using auto-discovery routines known in the art, or through manual user input. In some embodiments, processing circuits and/or medical devices can be configured to authenticate another processing circuit before connecting to it. This security authentication can comprise a handshake protocol, the sharing and acceptance of a shared secret, verification of the identity of a processing circuit with a trusted authority, or any other authentication mechanism known in the art. Once a processing circuit is "paired" or connected with a medical device or system, the processing circuit, as well as the timing circuit associated with that processing circuit, can be configured to start communicating with the other processing circuits and/or timing circuits on the medical device or system.

Enterprise environment 230 can comprise multiple processing circuits as well. For example, enterprise environment can comprise blood pressure sensor circuit 231, ECG circuit 232, records circuit 234, ventilator circuit 235, and drug delivery circuit 236. Some of these processing circuits can perform substantially the same functions as processing circuits that exist in the mobile environment 200—for example, ventilator circuit 235 can perform substantially the same function as ventilator circuit 221. A patient arriving at a hospital can therefore be handed off from one processing circuit (e.g., a first ventilator circuit) associated with one device to another processing circuit (e.g., a second ventilator circuit) associated with another, separate device. Thus, as part of the flow of patient care, processing circuits from separate devices may be synchronized with each another to provide seamless monitoring and/or treatment from location to location.

As illustrated in FIG. 1, each of the processing circuits in FIG. 2, regardless of whether they are deployed in mobile environment 200 or enterprise environment 230, can be configured to communicate with at least one other processing circuit (and possibly all processing circuits) via a network 250. The network 250 can be configured in all of the ways discussed above in relation to network 150 in FIG. 1. Each of the processing circuits can also comprise a timing circuit configured to communicate with at least one other timing circuit to coordinate timing among the processing circuits. For instance, defibrillator circuit 211 can include a timing circuit 211$b$, while ECG circuit 212 can include timing circuit 212$b$, etc.

Figure 3A:
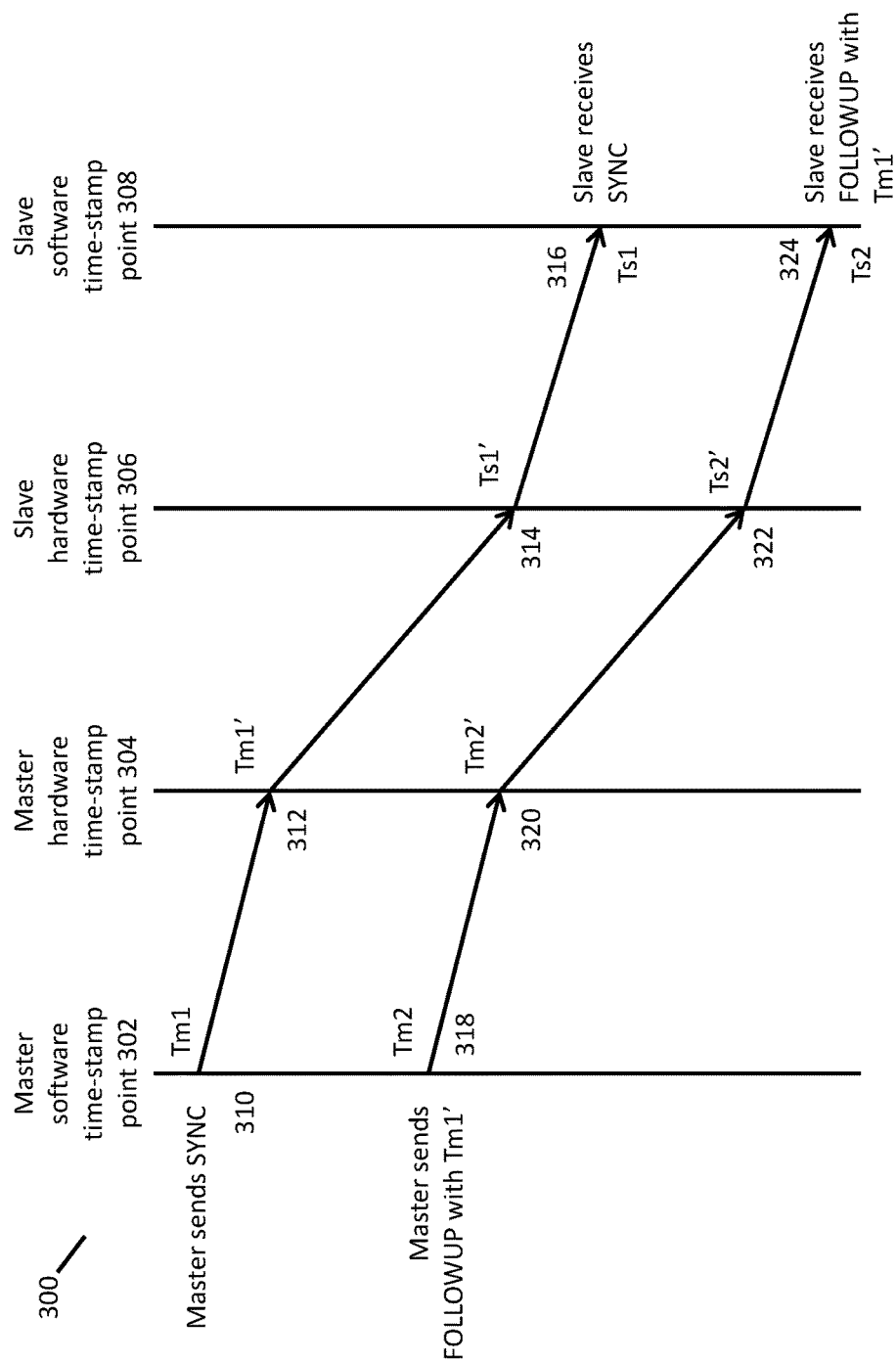
FIGS. 3A and 3B are signal flow diagrams illustrating an exemplary signal flow for coordinating timing between a master timing circuit and a slave timing circuit, according to some embodiments.
Figure 3B:
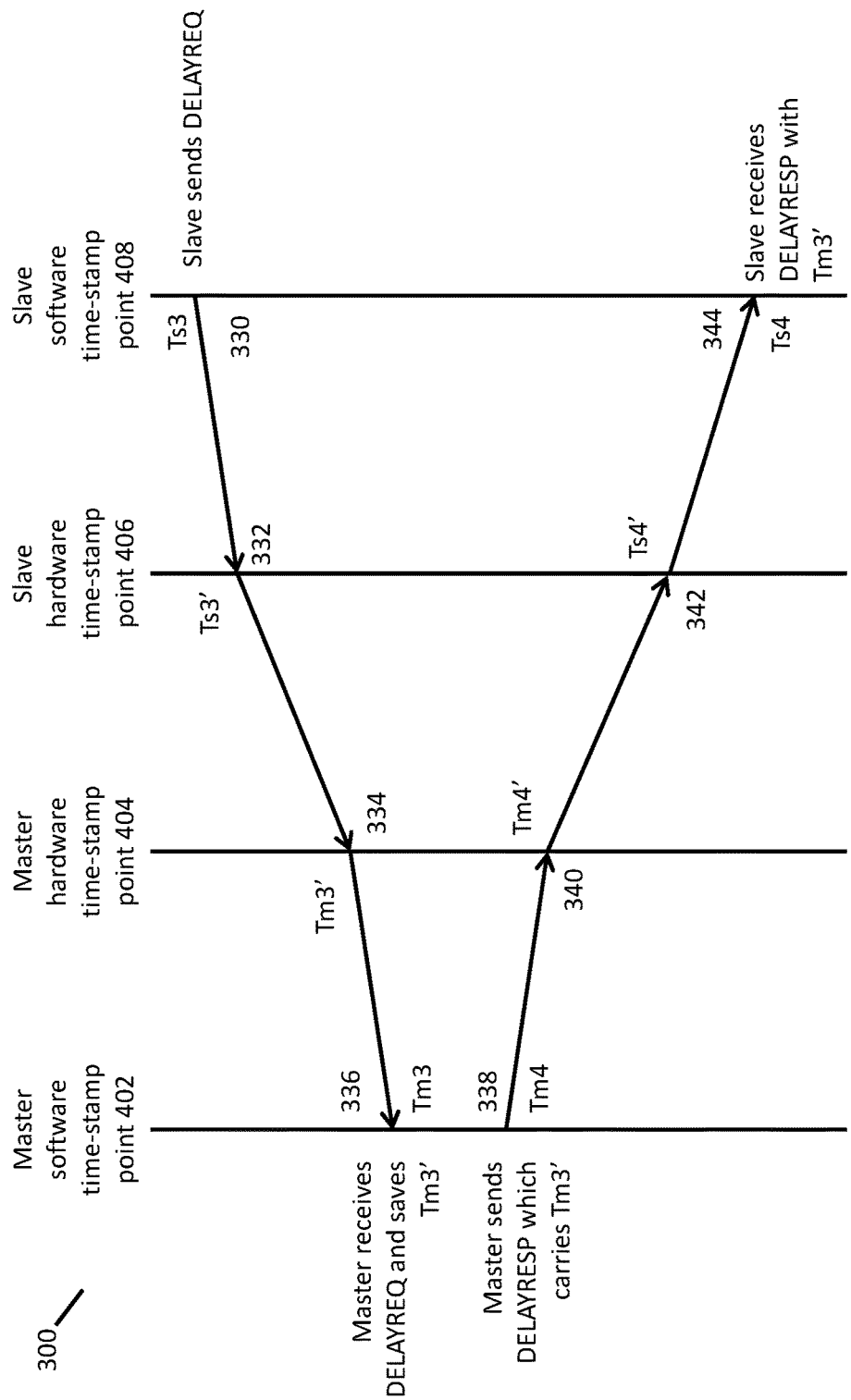

FIGS. 3A and 3B are signal flow diagrams illustrating an exemplary signal flow 300 for coordinating timing between a "master" timing circuit that keeps a globally "correct" time, and a "slave" timing circuit that synchronizes to the master timing circuit's local clock, according to some embodiments.

In some embodiments, the medical system can utilize a timing protocol to coordinate timing between master timing circuits and slave timing circuits. Examples of such timing protocols can include the IEEE 1588 or Precision Time Protocol (PTP), the Network Time Protocol (NTP), the Clock Sampling Mutual Network Synchronization (CS-MNS) algorithm, the Reference Broadcast Synchronization (RBS) algorithm, the Reference Broadcast Infrastructure Synchronization (RBIS) algorithm, and the Global Positioning System (GPS). The IEEE 1588-2008 Standard for Precision Clock Synchronization Protocol for Networked Measurement and Control Systems is incorporated by reference herein in its entirety. The IEEE 1588 protocol is also described in further detail in Jones, Mike, "Get in Sync!: IEEE 1588v2 Transparent Clock Benefits for Industrial Control Distributed Networks," Micrel, Inc. (Mar. 22, 2012), and from Wu, Jiang and Peloquin, Robert, "Synchronizing Device Clocks Using IEEE 1588 and Blackfin Embedded Processors," Analog Dialogue 43-11 (November 2009), both of which are incorporated by reference herein in their entirety.

IEEE 1588 is a precision time protocol typically used to synchronize clocks in multiple distinct devices across a geographically dispersed network, and is not generally used to coordinate timing within a single device. This is because single devices are commonly operated using a single common clock, and therefore do not need multiple processing circuits with distinct local clocks. Furthermore, single devices generally do not employ an internal signaling network, such as an Ethernet network. Such a signaling network requires significant signaling overhead as well as dedicated hardware and software which can increase the cost and complexity of single devices. Instead, single devices generally use a standard control bus to allow components to communicate with one another (e.g., simple serial interfaces such as UART, I2C, and SPI or higher speed and complexity USB technology), and can also share certain common resources, such as a shared memory and/or processors to facilitate easier communication with less overhead. In the case of medical systems using the techniques described herein, however, it can be advantageous to separate out tasks across multiple, separate processing circuits for the power distribution, security, computational efficiency, and/or cost reasons discussed above. It can also be advantageous to utilize an internal signaling network to allow components within a single device to be readily swapped in or out with replacement or complementary components, or to allow a device to interface readily with external devices, such as those in mobile environment 200 or enterprise environment 230. By using an internal signaling network, a first processing circuit's interactions with a second processing circuit can be standardized regardless of whether the two processing circuits are integrated into the same device, are connected via a short-range wireless or wired communication link, or even geographically dispersed. As a result, while precision time protocols such as IEEE 1588 are not normally used in such contexts, they can be advantageously employed in the medical system context using the techniques described herein.

As discussed above, each timing circuit can include a local clock. Each timing circuit can also include a software layer as well as a hardware layer. To illustrate this, FIGS. 3A and 3B include four time-stamp points: master software time-stamp point 302, master hardware time-stamp point 304, slave hardware time-stamp point 306, and slave software time-stamp point 308. The software layer of a timing circuit can record a time-stamp, according to the local clock of that timing circuit, corresponding to the time at which an instruction is sent to the hardware layer to send a message to another timing circuit. The software layer can also record a time-stamp, according to the local clock of that timing circuit, corresponding to the time at which the software layer processes a message received via the hardware layer from another timing circuit. The hardware layer of a timing circuit can also record a time-stamp according to when a message is actually sent to another timing circuit, as well as to record a time-stamp according to when a message is actually received from another timing circuit. By enabling the hardware layer of a timing circuit to record time-stamps according to the timing circuit's local clock, timing errors associated with delays or other latency from processing of software instructions, such as process threading or queueing issues, can be diminished. For example, the system may account for time differences that arise due to a number of factors, such as disparity between time-stamp signals of each of the timing circuits and/or communications latency between respective timing/processing circuits as signals travel back and forth.

While time differences between clocks of timing circuits may be determined as part of the synchronization, it can be appreciated that an accurate measure of the communications latency may be sufficient for timing circuits to be substantially synchronized. For example, the receiving timing circuit, or other communications unit, may shift the received data by the amount dictated by the communications latency to synchronize with a local data stream. In some cases, time stamping and calculation of time difference between timing circuits may be provided as a secondary or redundant measure of synchronization.

At point 310, the software layer of the master timing circuit instructs the hardware layer of the master timing circuit to send a synchronization or "SYNC" message. The time at which the software of the master timing circuit issues this instruction is time-stamped and saved as time Tm1, according to the master timing circuit's local clock. At point 312, the hardware layer of the master timing circuit executes this instruction by sending the SYNC message, and time-stamps and saves the time at which this happens as time Tm1', again according to the master timing circuit's local clock. The SYNC message propagates through the network connecting the master timing circuit to the slave timing circuit and is received by the hardware layer of the slave timing circuit at point 314. The slave timing circuit time-stamps and saves the time at which the SYNC message is received as time Ts1', according to the slave timing circuit's local clock. At point 316, the software layer of the slave timing circuit begins processing the received SYNC message, and time-stamps and saves the time at which this occurs as time Ts1.

At a later point in time 318, the software layer of the master timing circuit instructs the hardware layer of the master timing circuit to send a FOLLOWUP message. The time at which the software of the master timing circuit issues this instruction is time-stamped and saved as time Tm2, according to the master timing circuit's local clock. The FOLLOWUP message can include the previously saved time-stamp Tm1'. At point 320, the hardware layer of the master timing circuit executes this instruction by sending the FOLLOWUP message, and time-stamps and saves the time at which this happens as time Tm2', again according to the master timing circuit's local clock. The FOLLOWUP message propagates through the network connecting the master timing circuit to the slave timing circuit and is received by the hardware layer of the slave timing circuit at point 322. The slave timing circuit time-stamps and saves the time at which the FOLLOWUP message is received as time Ts2', according to the slave timing circuit's local clock. At point 324, the software layer of the slave timing circuit begins processing the received FOLLOWUP message (including Tm1'), and time-stamps and saves the time at which this occurs as time Ts2.

Continuing on to FIG. 3B, at point 330, the software layer of the slave timing circuit instructs the hardware layer of the slave timing circuit to send a Delay Request or "DELAYREQ" message back to the master timing circuit. The time at which the software of the slave timing circuit issues this instruction is time-stamped and saved as time Ts3, according to the slave timing circuit's local clock. At point 332, the hardware layer of the slave timing circuit executes this instruction by sending the DELAYREQ message, and time-stamps and saves the time at which this happens as time Ts3'. The DELAYREQ message propagates through the network connecting the slave timing circuit to the master timing circuit and is received by the hardware layer of the master timing circuit at point 334. The master timing circuit time-stamps and saves the time at which the DELAYREQ message is received as time Tm3', according to the master timing circuit's local clock. At point 336, the software layer of the master timing circuit begins processing the received DELAYREQ message, and time-stamps and saves the time at which this occurs as time Tm3.

At a later point in time 338, and in response to the DELAYREQ message, the software layer of the master timing circuit instructs the hardware layer of the master timing circuit to send a Delay Response or "DELAYRESP" message. The time at which the software of the master timing circuit issues this instruction is time-stamped and saved as time Tm4, according to the master timing circuit's local clock. The DELAYRESP message can include the previously saved time-stamp Tm3'. At point 340, the hardware layer of the master timing circuit executes this instruction by sending the DELAYRESP message, and time-stamps and saves the time at which this happens as time Tm4', again according to the master timing circuit's local clock. The DELAYRESP message propagates through the network connecting the master timing circuit to the slave timing circuit and is received by the hardware layer of the slave timing circuit at point 342. The slave timing circuit time-stamps and saves the time at which the DELAYRESP message is received as time Ts4', according to the slave timing circuit's local clock. At point 344, the software layer of the slave timing circuit begins processing the DELAYRESP message (including Tm3'), and time-stamps and saves the time at which this occurs as time Ts4.

By the end of process 300, the slave timing circuit is in possession of the following time-stamps: Ts1', Ts1, Ts2', Ts2, Tm1', Ts3, Ts3', Ts4', Ts4, and Tm3'. The slave timing circuit can then calculate two values: a "delay" value representing the amount of time by which the slave timing circuit's local clock differs from the master timing circuit's local clock, and an "offset" value representing the average amount of time required to send a message from the master timing circuit to the slave timing circuit, and vice versa. Assuming that communications delays are symmetric, i.e., the amount of time required to send a message from the master to the slave is the same as the amount of time required to send a message from the slave to the master, the delay can be calculated using the following formula (Equation 1):

$$\text{Delay} = \frac{(Ts1' - Tm1') + (Tm3' - Ts3')}{2}$$

Similarly, the offset can be calculated using the following formula (Equation 2):

$$\text{Offset} = \frac{(Tm3' - Ts3') - (Ts1' - Tm1')}{2}$$

The slave timing circuit is now aware of the amount of time by which its local clock is out-of-sync with the local clock of the master timing circuit. The slave timing circuit can use this delay value to calibrate and adjust its own local clock so that it is more in-sync with the master timing circuit. In some embodiments, the slave timing circuit can do so simply by adding or subtracting the calculated delay from the current time on its local clock. This method, however, can cause the slave timing circuit's local clock to exhibit undesirable jitter. Alternatively, the slave timing circuit can implement a feedback control loop using the master-clock time as the reference command, the slave-clock time as the output tracking the master-clock time, and their time difference to drive the slave timing circuit's adjustable clock. For example, the slave timing circuit can implement a proportional-integral-derivative (PID) controller to track the master timing circuit's local clock accurately, while reducing clock jitter. In some embodiments, the slave timing circuit can also output an indication representative of the offset value or the delay value to a medium for user review. For instance, the slave timing circuit can output the offset value or the delay value, or a parameter derived from the offset value or the delay value (e.g., a running average, a time-weighted average that favors more recent values over older values, etc.) to a medium such as a screen, a speaker, a network interface, and/or a log maintained in volatile or non-volatile memory. As discussed above, the disclosed techniques can achieve sub-microsecond-level synchronization between multiple timing circuits.

Further provided herein, as medical-related information is substantially synchronized between processing circuits, the system may account for communications latency that arises as signals travel between timing and/or processing circuits. In some cases, as circuits send signals back and forth, the elapsed time corresponding to those signals, which may result in such latency, may vary. Accordingly, it may be beneficial to periodically update the overall communications latency between circuits, for example, as averaged over suitable time intervals. Such updates may be dynamic as the time delay between circuits may change. For instance, medical data may be received at slightly different sampling rates, which may contribute to overall time lag between channels. As an illustrative example, the sampling rates at successive points in time (e.g., second 1, second 2, second 3, etc.) may be received over a range of, for example, between 250.0 Hz and 250.5 Hz and, at any given time depending on the conditions of communication, may vary to another range, such as between 250.2 Hz and 251.2 Hz (or another possible range). Hence, the system may account for any such disparity in latency existing in the communication channel(s). In some implementations, one or more of the circuits may have the ability to communicate via two or more communication channels. One of the two or more channels may be a hardware-based communication such as Ethernet, or other serial or parallel hardware communication with low latency, and a second channel with a higher latency. The higher latency channel may be a wireless communication channel such as Zigbee or WiFi. In one configuration, one circuit may be plugged into a second circuit using a USB, PCMIA, or other hardware connectors. The communication latency is measured initially when communication is established between the circuits, and then at regular intervals, such as every 1, 10, 20 or 60 seconds. If the units are disconnected during use, communications may be automatically re-established via the wireless channel, and as soon as communications are established, a new process is triggered for measuring the communication latency. The initiation of a measurement of communication latency may occur at regular intervals such as those listed above, or may be triggered by events such as the detection of a circuit being disconnected, or an increase of the measured bit-error-rate (BER) increasing above a threshold.

In some embodiments, the communications latency may be periodically or continually updated so that the amount of error due to variation in the communication latency time may be taken into account in evaluating the overall reliability of the medical information. For instance, the time synchronization accuracy may be presented as a measure of the time jitter of the latency measurement. The jitter measure may be a statistical measure such as one standard deviation, three standard deviations, etc. The jitter error may be displayed as a number or graphical element such as a horizontal bar during system use, or afterward when the collected data streams are being displayed together in a post-case review, such as with ZOLL CodeReview software (available from ZOLL Medical Corporation, located in Chelmsford Mass.).

In some embodiments, an indication of the expected time error (e.g., communications latency averaged over a suitable period of time, or otherwise statistically estimated) may be provided along with other information (e.g., time stamps) as timing circuits send requests and responses to one another. For example, in some cases, this estimated communications latency or the variation in the latency between circuits may be output to a data file, display or other medium for a user/operator to review so as to understand the overall reliability of the data. Accordingly, when evaluating medical data (e.g., ECG, heart/lung sounds, contractility motion, ETCO2, other physiological parameters and/or medical communications), the user/operator may be able to better distinguish between real data and noise.

Figure 4:
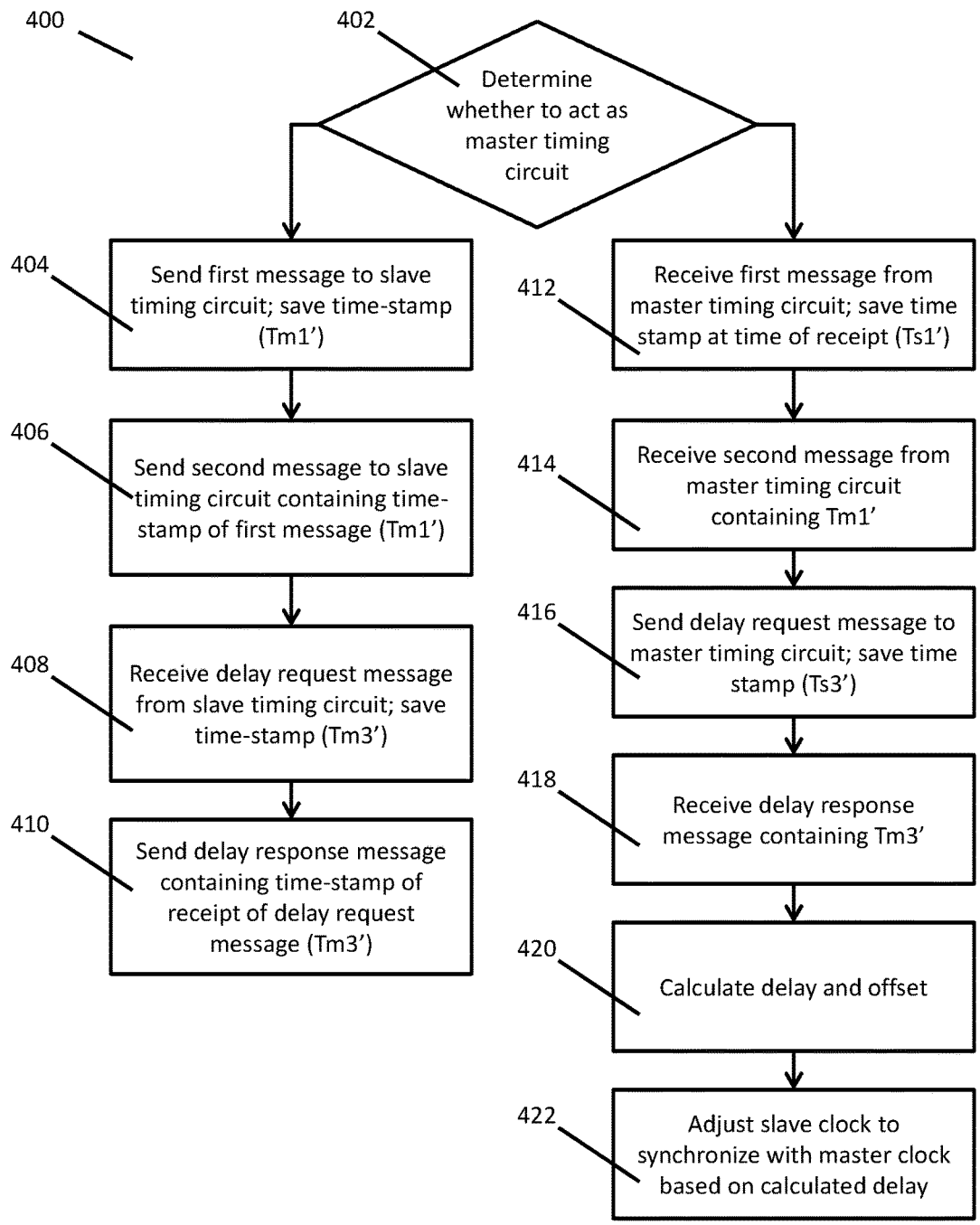
FIG. 4 is a flowchart illustrating an exemplary process for coordinating timing among a plurality of timing circuits, according to some embodiments.

FIG. 4 is a flowchart illustrating an exemplary process 400 for coordinating timing among a plurality of timing circuits, according to some embodiments. As discussed above, each timing circuit can include a local clock. At step 402, each timing circuit first determines whether it should act as a "master" timing circuit that keeps the global, "correct" time, or a "slave" timing circuit that synchronizes to the master timing circuit's local clock. Preferably, the timing circuit having the most accurate local clock should be selected to operate as the "master" timing circuit. For example, timing circuits having access to a GPS clock or other highly accurate network clock, or incorporating a highly accurate time-keeping mechanism, should preferably be selected as the master timing circuit. In some embodiments, each timing circuit can determine whether it should act as a "master" or a "slave" timing circuit according to pre-defined software or hardware settings that will cause it to always act as a timing circuit of a certain type. In other embodiments, each timing circuit can communicate accuracy information (e.g., expected amount of timing error within a certain time period) and/or attribute information (e.g., type of time-keeping mechanism used) with other timing circuits. Each timing circuit can then use a best clock selection algorithm to determine whether to act as a "master" or a "slave" timing circuit. Since each timing circuit can be configured to use the same best clock selection algorithm, there would preferably be only one timing circuit selected as the "master" timing circuit in every case. In some cases, the addition of a timing circuit to an existing medical system can cause a switch in which timing circuit acts as the master timing circuit if the best clock selection algorithm determines that the newly added timing circuit has a more accurate local clock than any of the other pre-existing timing circuits. In other embodiments, timing circuits can be configured to measure the accuracy and drift of other timing circuits' local clocks over a trial period, and then select the timing circuit exhibiting the lowest timing error as the master timing circuit. In yet other embodiments, the master timing circuit can be randomly selected—this can be advantageous in cases where every timing circuit is expected to exhibit the same or similar timing accuracies.

If a timing circuit determines to act as a master timing circuit, process 400 can branch to step 404. At step 404, the master timing circuit can send a first message (e.g., a SYNC message) to a slave timing circuit via a network. The master timing circuit can also save the time-stamp at which this SYNC message is sent (Tm1'), according to the local clock of the master timing circuit. At step 406, the master timing circuit can send a second message (e.g., a FOLLOWUP message) to the slave timing circuit via the network. This second message can include the time-stamp of the first message (Tm1'). At step 408, the master timing circuit can receive a delay request message from the slave timing circuit, and save the time-stamp at which this delay request message is received (Tm3'), according to the local clock of the master timing circuit. At step 410, in response to the delay request message, the master timing circuit can send a delay response message to the slave timing circuit containing the time-stamp corresponding to its receipt of the delay request message (Tm3').

If a timing circuit determines to act as a slave timing circuit, process 400 can branch to step 412. At step 412, the slave timing circuit can receive a first message (e.g., a SYNC message) from a master timing circuit via a network. The slave timing circuit can also save the time-stamp at which this SYNC message is received (Ts1'), according to the local clock of the slave timing circuit. At step 414, the slave timing circuit can receive a second message (e.g., a FOLLOWUP message) from the master timing circuit via the network. This second message can include the time-stamp at which the first message had been sent by the master timing circuit (Tm1'), according to the local clock of the master timing circuit. At step 416, the slave timing circuit can send a delay request message to the master timing circuit, and save the time-stamp at which this delay request message is sent (Ts3'). At step 418, the slave timing circuit can receive a delay response message from the master timing circuit via the network. The delay response message can contain the time-stamp at which the delay request message was received at the master timing circuit (Tm3'), according to the local clock of the master timing circuit. At step 420, the slave timing circuit can calculate values for delay and offset according to equations (1) and (2) above. And at step 422, the slave timing circuit can adjust its local clock to synchronize with the local clock of the master timing circuit.

The signal flows and processes described above in relation to FIGS. 3A, 3B and 4 are exemplary only, and many modifications are possible. For example, instead of sending a FOLLOWUP message after the SYNC message containing Tm1', the master timing circuit can include Tm1' as part of the SYNC message itself. This approach may potentially require more sophisticated hardware and/or software at the master timing circuit, but would have the advantage of reducing the necessary signal traffic between the master timing circuit and the slave timing circuit. Alternatively, the above signal flows and processes can be simplified by not differentiating between the software and the hardware layers of the master and the slave timing circuits, and simply using one set of timestamps (either at the software or the hardware level). This can have the disadvantage of introducing additional timing errors due to processing time, but may be easier and more economical to implement.

Figure 5A:
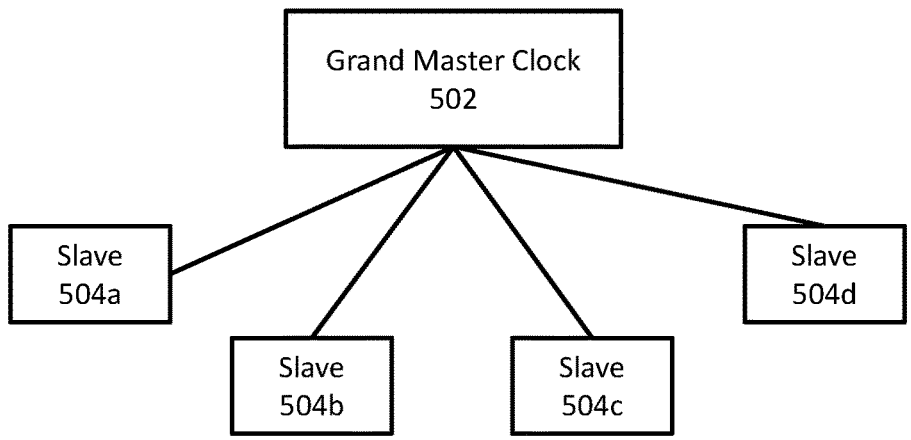
FIGS. 5A and 5B illustrate two potential network architectures for a medical system, according to some embodiments.
Figure 5B:
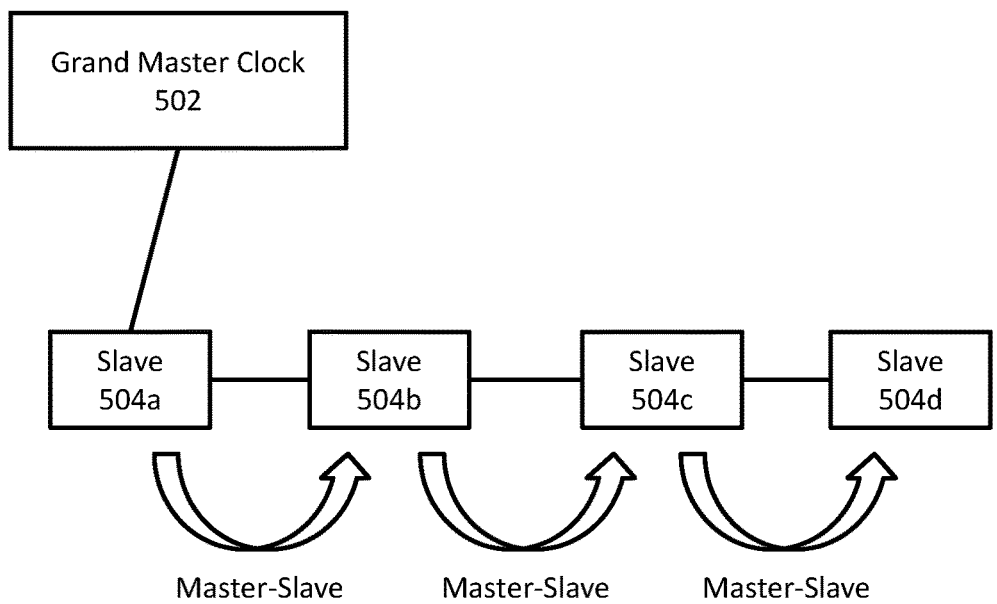

Multiple ways of connecting a master timing circuit to a plurality of slave timing circuits are possible. FIGS. 5A and 5B illustrate two potential network architectures. In FIG. 5A, a "grandmaster" timing circuit 502 can be connected to a plurality of slave timing circuits 504a, 504b, 504c, and 504d according to a hub-and-spoke architecture. Messages such as SYNC, FOLLOWUP, DELAYREQ, and DELAYRESP can be sent directly between the grandmaster timing circuit 502 and each of the slave timing circuits 504a-d. In contrast, FIG. 5B illustrates a "daisy-chain" architecture, whereby a "grandmaster" timing circuit 502 is connected only to a first slave timing circuit 504a. Slave timing circuit 504a can in turn be connected to slave timing circuit 504b, which in turn can be connected to 504c, which in turn can be connected to slave timing circuit 504d. "Grandmaster" timing circuit 502 can act as a master timing circuit for slave circuit 504a. Slave timing circuit 504a can in turn act as a master timing circuit for slave timing circuit 504b. And slave timing circuit 504b can act as a master timing circuit for 504c, which in turn can act as a master timing circuit for 504d. This network architecture can simplify the network connections in a medical system and reduce the computational burden of grandmaster timing circuit 502, but can also cause accumulation of timing errors for each successive slave timing circuit 504a-d as one traverses further down the chain of connections. In yet other embodiments, "grandmaster" timing circuit 502 can be connected to each of slave timing circuits 504a-d using the same architecture as illustrated in FIG. 5B, but can still act as the master timing circuit for each slave. For example, SYNC, FOLLOWUP, DELAYREQ, and DELAYREQ messages can still be sent directly from the "grandmaster" timing circuit 502 to each slave timing circuit via other slave timing circuits, and the delay incurred in forwarding each message can simply be accounted for as a larger "offset" time in Equation (2) above. A combination of the architectures illustrated in FIGS. 5A and 5B are also possible, whereby a "grandmaster" timing circuit 502 is connected to a plurality of slave timing circuits, which in turn are connected to other slave timing circuits further down the chain. The present disclosure is not limited to any particular network architecture.

Integrating timing circuits into the processing circuits of a medical system can facilitate substantial synchronizations of processing circuits, which in turn can facilitate applications for which tight time synchronization is required. In some embodiments, substantial synchronization of processing circuits may involve time synchronizations of less than 1 millisecond, less than 900 microseconds, less than 800 microseconds, less than 700 microseconds, less than 600 microseconds, less than 500 microseconds, less than 400 microseconds, less than 300 microseconds, less than 200 microseconds, less than 100 microseconds, or even less. In some embodiments, substantial synchronization of processing circuits may involve time synchronizations of 50 microseconds or less (e.g., 1-50 microseconds, 1-20 microseconds, etc.). In yet other embodiments, substantial synchronization of processing circuits may involve time synchronizations of 10 microseconds or less (e.g., 1-10 microseconds, 1-5 microseconds, etc.). For more precise embodiments, time synchronizations of less than one microsecond between processing circuits can be achieved. FIGS. 6A, 6B, 6C, and 6D illustrate certain exemplary use cases to which the disclosed time synchronization scheme can be applied.

FIG. 6A illustrates how an ECG sensor processing circuit 604 can be synchronized and combined with an ultrasound sensor processing circuit 606, according to some embodiments. ECG sensor circuit 604 can be configured to generate an ECG waveform corresponding to a patient, whereas an ultrasound sensor circuit 606 can be configured to output an ultrasound image of a part of or all of a patient's body, such as the patient's heart. The output of ECG sensor circuit 604 can be combined with the moving ultrasound image/video of ultrasound sensor circuit 606 by a processor 602 in order to generate a visual display showing an ECG trace synchronized with an ultrasound video image. The combined, synchronized display can be useful for showing exactly how the patient's heart physically moves in response to detected electrical signals on the ECG, which can be useful for diagnostic or treatment purposes. While FIG. 6A shows an ECG sensor circuit 604 combined with an ultrasound sensor circuit 606, an ECG sensor circuit can also be combined with other types of sensor circuits and outputs, such as an indication of the patient's heartbeat (from a heartbeat monitor), an indication of the patient's breathing pattern (from a breathing sensor), an indication of the patient's blood pressure (from a blood pressure monitor), etc. In general, the disclosed methods, systems and apparatus for coordinating timing between multiple processing circuits can be used where two or more physiological statuses of a patient need to be displayed at the same time and in a synchronized manner. This can be useful where these two or more physiological statuses need to be compared to aid in diagnosis or treatment.

FIG. 6B illustrates how an ECG sensor processing circuit 604 can be synchronized and combined with an accelerometer processing circuit 610, according to some embodiments. As discussed above, ECG sensor circuit 604 can be configured to generate an ECG waveform corresponding to a patient. If the patient is moving, however, such as if the patient is being transported by a moving vehicle (e.g., an ambulance), or if the patient is shivering, walking, subject to chest compressions applied during CPR, or otherwise in motion, the ECG waveform output by the ECG sensor circuit 604 can exhibit undesirable motion artifacts, i.e., inaccuracies introduced by motion or acceleration that can obscure or distort the patient's ECG waveform. By using accelerometer circuit 610 to measure an acceleration associated with the patient, processor 602 can filter out and/or compensate for such motion artifacts in the ECG waveform output by the ECG sensor circuit 604. Synchronizing the local clocks of the ECG sensor circuit 604 and the accelerometer circuit 610 can improve the extent to which such filtering and/or compensation techniques can remove motion artifacts. Achieving sub-microsecond-level synchronization between ECG sensor circuit 604 and accelerometer circuit 610 can be particularly advantageous for filtering out motion artifacts. A synchronized accelerometer can also be used to filter out motion artifacts in the outputs of other types of sensor circuits, such as a heartbeat monitor, an ultrasound, X-ray, CT, or other imaging sensor, and a blood pressure sensor. In general, the disclosed methods, systems and apparatus for coordinating timing between multiple processing circuits can be used to synchronize an accelerometer with another sensor circuit, so as to filter out and/or compensate for motion artifacts in the sensor circuit's output.

Figure 6D:
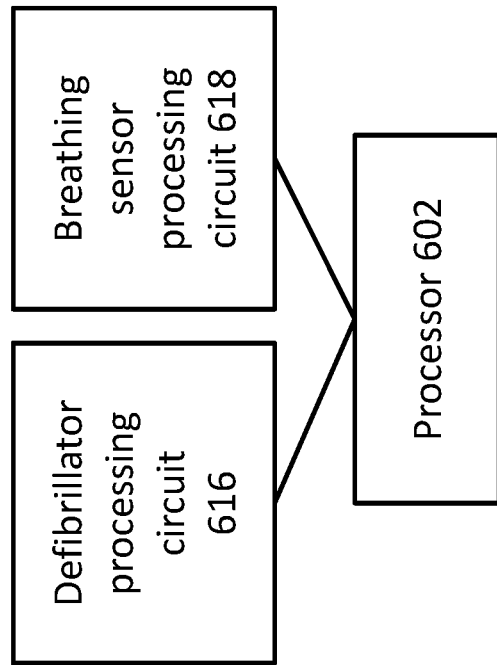
FIG. 6D illustrates how a defibrillator circuit can be synchronized and combined with a breathing sensor circuit, according to some embodiments.
Figure 6C:
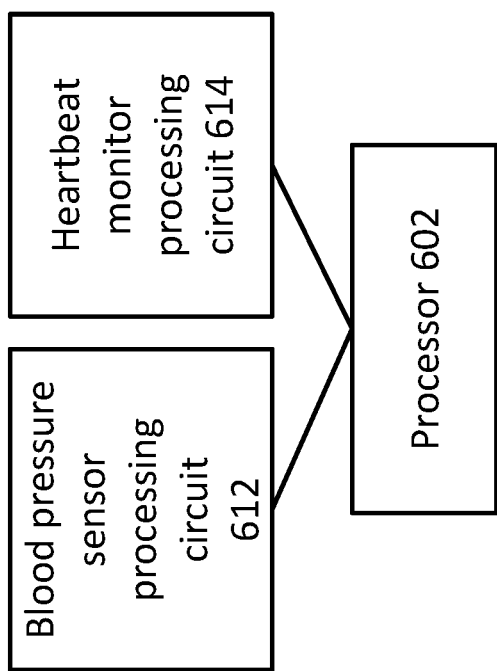
FIG. 6C illustrates how a blood pressure sensor circuit can be synchronized and combined with a heartbeat monitor, according to some embodiments.

FIG. 6C illustrates how a blood pressure sensor processing circuit 612 can be synchronized and combined with a heartbeat monitor processing circuit 614, according to some embodiments. FIG. 6C depicts blood pressure sensor circuit 612 and heartbeat monitor circuit 614 under the common control of a processor 602—however, other configurations in which blood pressure sensor circuit 612 and heartbeat monitor circuit 614 are in direct communication with one another are also possible. Blood pressure sensor circuit 612 can be configured to measure a patient's systolic blood pressure when the patient's heart beats, and also to measure a patient's diastolic blood pressure when the patient's heart is at rest. By synchronizing the local clocks of blood pressure sensor circuit 612 and heartbeat monitor 614, blood pressure sensor circuit 612 can be configured to measure the patient's systolic blood pressure at the precise instant when the patient's heart beats, rather than slightly before or slightly after the optimal measurement time. In particular, achieving sub-microsecond-level synchronization can be useful for diminishing errors in a patient's blood pressure reading.

FIG. 6D illustrates how a defibrillator processing circuit 616 can be synchronized and combined with a breathing sensor processing circuit 618, according to some embodiments. FIG. 6D depicts defibrillator circuit 616 and breathing sensor circuit 618 under the common control of a processor 602—however, other configurations in which defibrillator circuit 616 and breathing sensor circuit 618 are in direct communication with one another are also possible. It can sometimes be advantageous to deliver an electric shock from a defibrillator in-between a patient's breath. Breathing sensor circuit 618 can be configured to measure a patient's respiratory rate, and to determine when a patient is breathing and is not breathing. By synchronizing and combining breathing sensor circuit 618 with defibrillator circuit 616, defibrillator circuit 616 can be configured to deliver a therapeutic electric shock only at the optimal time, e.g., in-between a patient's breaths. In particular, achieving sub-microsecond-level synchronization can be useful for precisely timing the right moment to deliver a therapeutic electric shock. Other types of treatment circuits can be substituted for defibrillator circuit 616 and other types of sensor circuits can be substituted for breathing sensor circuit 618. In general, the disclosed systems, methods and apparatus for coordinating timing between multiple processing circuits can be used to facilitate the delivery of a treatment (e.g., delivery of a drug, operation of a ventilator, or delivery of a therapeutic electric shock) at optimal times.

Figure 6E:
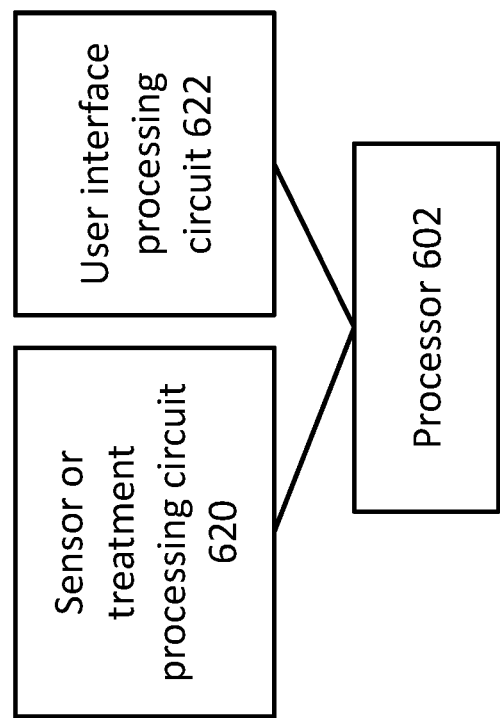
FIG. 6E illustrates how a defibrillator circuit can be synchronized and combined with a sensor or treatment circuit, according to some embodiments.

FIG. 6E illustrates how a sensor or treatment processing circuit 620 can be synchronized and combined with a user interface processing circuit 622, according to some embodiments. Sensor or treatment circuit 620 can comprise any type of sensor configured to sense a physiological status of the patient, including the patient's breathing, heartbeat, spectral muscle-chemistry, ECG, end-tidal carbon dioxide, blood pressure, etc. Sensor or treatment circuit 620 can also comprise a sensor configured to sense other parameters relevant to the condition or treatment of the patient, such as the ambient environment around the patient (e.g., the ambient temperature, an acceleration associated with the patient's environment), or the condition of medical equipment associated with the patient (e.g., the battery charge of a medical device attached to the patient). In some embodiments, sensor or treatment circuit 620 can also comprise a medical device configured to administer a treatment to the patient, such as a breathing regulator, a defibrillator or AED, a drug delivery device, etc. With the aid of processor 602, sensor or treatment circuit 620 (or other processing circuit) can be time synchronized with user-interface circuit 622 via a dynamically secure and reconfigurable network. In some embodiments, the user-interface circuit 622 can provide for real-time monitoring of the patient's condition, environment, or associated equipment. In other embodiments, user-interface circuit 622 can provide real-time instructions to sensor or treatment circuit 620 to begin, end, or adjust a treatment being administered to the patient. Time synchronization between sensor or treatment circuit 620 and user-interface circuit 622 can be important for ensuring that medical data generated by sensor or treatment circuit 620 is correctly displayed on user-interface circuit 622, and for ensuring that treatments are properly administered to the patient.

In embodiments where user-interface circuit 622 is located at a remote location relative to sensor circuit 620, user-interface circuit 622 can allow for remote monitoring from a distance.

As discussed above, the processing circuits may be time synchronized in a manner so as to form a secure network that is dynamically reconfigurable. This manner of time synchronization may be advantageous when applied to emergency/rescue scenarios which often employ multiple devices (e.g., medical devices, monitors, defibrillators, controllers, user interfaces, communications devices, etc.) in communication with one another where precision signaling (e.g., updating, reporting, input/output, control) is preferable. In some embodiments, such devices may include one or more defibrillators/monitors and/or other devices (e.g., user-specific devices, tablets, wrist-worn apparatuses, feedback devices, amongst others) in mutual communication, which may require a secure network connection there between, for example, so that information originating from one device is appropriately transmitted or otherwise provided specifically to another device without information loss, or data breach.

Though, in environments that are often chaotic and fast paced, such devices may also be quickly reconfigurable and able to seamlessly move in and out of the secure network without requiring substantial user action. That is, rather than requiring a user to potentially spend significant amounts of time in manually configuring the system of each device in the network, devices located at the emergency scene may be pre-configured to dynamically join and/or leave the secure network, for example, automatically and/or with one or more simple actions (e.g., switch actuation, pressing a button, near field communication connection, radio frequency, location/proximity recognition, gestural code, amongst others). Such devices may further be time synchronized according to methods described herein.

In various embodiments, the time synchronization protocol may carry through as various modes of communication may shift between devices. For instance, medical devices may be hot swappable in that one may be directly connected (e.g., plugged in) to another, yet when they are physically disconnected, the mode of communication may shift to a wireless form, such as Ethernet, Bluetooth, Near Field, etc. When the mode of communication shifts, the devices may initiate a suitable request and response loop test, such as those discussed herein, that checks the timing there between.

Aspects of the present disclosure may also apply during an entire rescue sequence, such as from an emergency site to a hospital. For example, a portable defibrillator or monitoring device located in a home may be initially connected to a wireless Internet network. Though, when transported to an ambulance, truck or hospital, the defibrillator or monitoring device may automatically time synch with nearby devices, such as more advanced life support devices and/or mobile devices (e.g., tablet, cell phone) that employ medical capabilities. As the patient moves along within the emergency resuscitation context, the medical devices encountered or otherwise associated therewith may seamlessly employ time synching capabilities between operating and timing circuits, as discussed herein.

Some embodiments of the present disclosure include various steps, some of which may be performed by hardware components or may be embodied in machine-executable instructions. These machine-executable instructions may be used to cause a general-purpose or a special-purpose processor programmed with the instructions to perform the steps. Alternatively, the steps may be performed by a combination of hardware, software, and/or firmware. In addition, some embodiments of the present disclosure may be performed or implemented, at least in part (e.g., one or more circuits), on one or more computer systems, mainframes (e.g., IBM mainframes such as the IBM zSeries, Unisys ClearPath Mainframes, HP Integrity NonStop servers, NEC Express series, and others), or client-server type systems. In addition, specific hardware aspects of embodiments of the present disclosure may incorporate one or more of these systems, or portions thereof.

Figure 7:
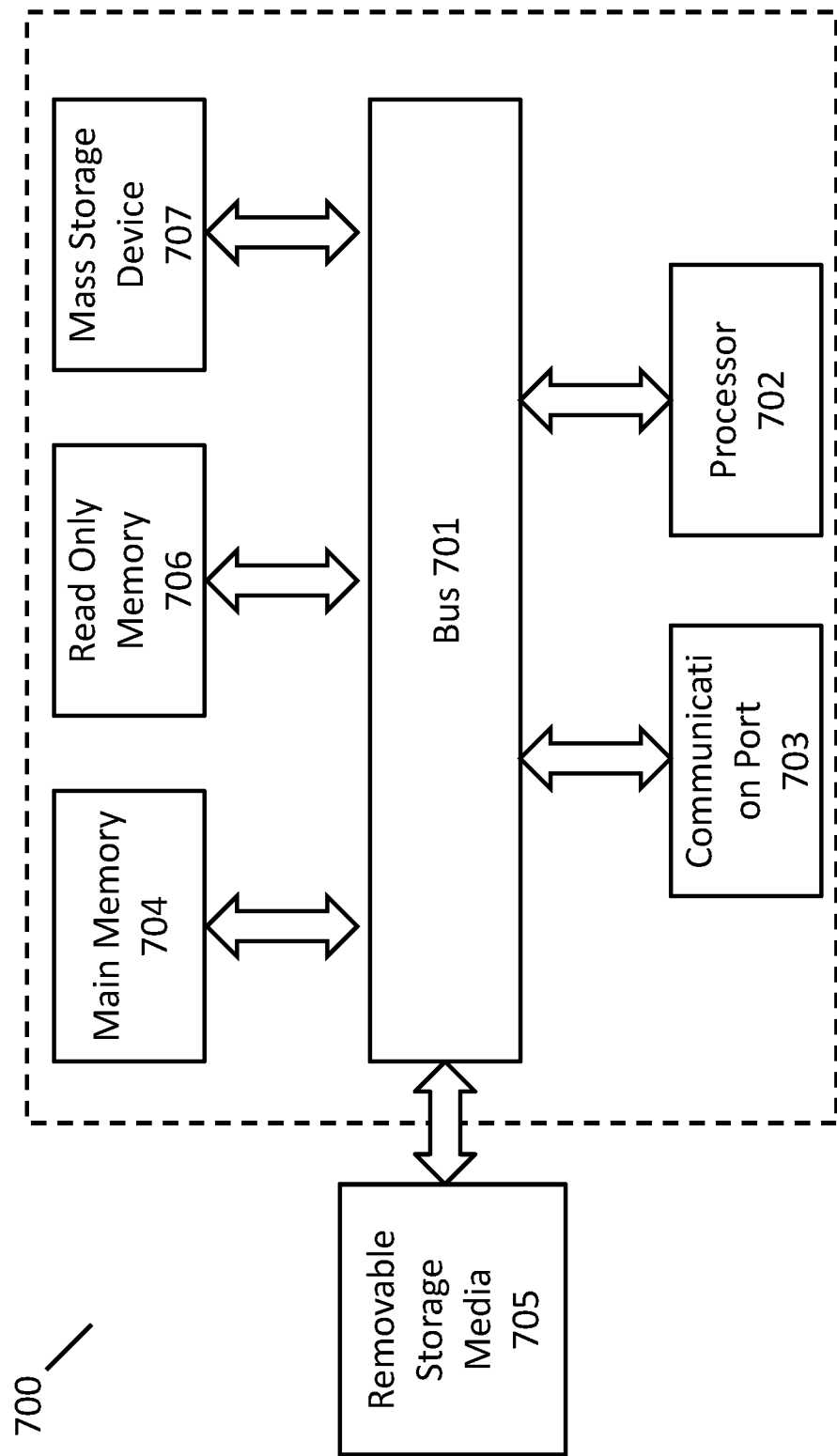
FIG. 7 depicts an exemplary computer system with which embodiments of the present disclosure may be utilized, according to some embodiments.

As such, FIG. 7 is an example of a computer system 700 with which embodiments of the present disclosure may be utilized. According to the present example, the computer system includes a bus 701, at least one processor 702, at least one communication port 703, a main memory 704, a removable storage media 705, a read only memory 706, and a mass storage 707.

Processor(s) 702 can be any known processor, such as, but not limited to, an Intel® Itanium® or Itanium 2® processor (s), an AMD® Opteron® or Athlon MP® processor(s), or Motorola® lines of processors. Communication port(s) 703 can be any of RS-232 port for use with a modem based dialup connection, a 10/100 Ethernet port, or a Gigabit port using copper or fiber, or wireless communication ports using, for example, WiFi, LTE, 3GPP, Bluetooth, NFC, or other wireless protocols. Communication port(s) 703 may be chosen depending on a network such as a Local Area Network (LAN), Wide Area Network (WAN), or any network to which the computer system 700 connects. Main memory 704 can be Random Access Memory (RAM), or any other dynamic storage device(s) commonly known to one of ordinary skill in the art. Read only memory 706 can be any static storage device(s) such as Programmable Read Only Memory (PROM) chips for storing static information such as instructions for processor 702, for example.

Mass storage 707 can be used to store information and instructions. For example, hard disks such as the Adaptec® family of SCSI drives, an optical disc, an array of disks such as RAID (e.g., the Adaptec family of RAID drives), or any other mass storage devices may be used, for example. Bus 701 communicably couples processor(s) 702 with the other memory, storage and communication blocks. Bus 701 can be a PCI/PCI-X or SCSI based system bus depending on the storage devices used, for example. Removable storage media 705 can be any kind of external hard-drives, floppy drives, flash drives, IOMEGA® Zip Drives, Compact Disc-Read Only Memory (CD-ROM), Compact Disc-Re-Writable (CD-RW), or Digital Video Disk-Read Only Memory (DVD-ROM), for example. The components described above are meant to exemplify some types of possibilities. In no way should the aforementioned examples limit the scope of the invention, as they are only exemplary embodiments.

The invention claimed is:

1. A medical system comprising:
a plurality of processing circuits in communication with one another, each processing circuit configured to provide medical-related data;
a plurality of timing circuits, each timing circuit having a clock, wherein at least some of the timing circuits are each associated with a different processing circuit of the plurality of processing circuits, and wherein each timing circuit is configured to:
communicate with at least one other timing circuit;
produce at least one first time stamped signal for the respective timing circuit;
transmit the at least one first time stamped signal to the at least one other timing circuit;
determine a communication latency between timing circuits;
produce at least one second time stamped signal for the respective timing circuit, the at least one second time stamped signal comprising a time stamp associated with the at least one first time stamped signal; and
transmit the at least one second time stamped signal to the at least one other timing circuit; and
a processor configured to analyze the communication latency between timing circuits and adjust time-alignment of medical-related data from at least some of the plurality of processing circuits so as to synchronize the medical-related data provided from the at least some of the plurality of processing circuits based at least on the at least one first and second timed stamped signals.

2. The medical system of claim 1, wherein the processor is configured to determine time differences between the clocks of the timing circuits during communication of the processing circuits and correct for the time differences between the clocks.

3. The medical system of claim 1, wherein each timing circuit is further configured to correct for a time difference between the clock of the timing circuit and another timing circuit.

4. The medical system of claim 1, wherein the plurality of processing circuits include at least one sensor configured to monitor a physiological status of a patient and to generate a set of sensor data based on the physiological status.

5. The medical system of claim 4, wherein
the at least one sensor includes an electrocardiogram (ECG) sensor configured to generate one or more ECG waveforms, and
the at least one sensor further includes a second sensor comprising at least one of a heartbeat sensor configured to monitor a heartbeat of the patient, a blood oxygen sensor configured to monitor a blood oxygen level of the patient, a carbon dioxide sensor configured to monitor an end-tidal carbon dioxide level of the patient, and an ultrasound sensor configured to generate an ultrasound image of the patient, and
wherein the medical system further comprises a timing circuit associated with the second sensor and configured to be substantially synchronized with a timing circuit associated with the ECG sensor.

6. The medical system of claim 4,
wherein the at least one sensor includes a blood pressure sensor configured to monitor a blood pressure of the patient and a heartbeat monitor configured to monitor a heartbeat of the patient, and
wherein the medical system further comprises a timing circuit associated with the blood pressure sensor and configured to be substantially synchronized with a timing circuit associated with the heartbeat monitor, and wherein the blood pressure sensor is configured to record a systolic blood pressure measurement when the heartbeat monitor indicates that the patient's heart is beating.

7. The medical system of claim 4, wherein the at least one sensor includes an accelerometer configured to monitor an acceleration associated with the patient and to generate a set of sensor data based on the acceleration, and the processor is configured to modify at least one other set of sensor data to compensate for inaccuracies associated with the acceleration.

8. The medical system of claim 4, wherein the at least one sensor includes at least one of a blood pressure sensor, a heartbeat sensor, a blood oxygen sensor, a carbon dioxide sensor, an ultrasound sensor, an accelerometer, an electrocardiogram (ECG) sensor, a spectral muscle-chemistry sensor, a temperature sensor, a video-camera, and a microphone.

9. The medical system of claim 1, wherein each timing circuit is configured to communicate with at least one other timing circuit via a wired or optical serial communications network.

10. The medical system of claim 1, wherein each timing circuit is configured to communicate with at least one other timing circuit via a wireless network.

11. The medical system of claim 1, wherein the plurality of processing circuits, the plurality of timing circuits, and the processor are integrated into a single device.

12. The medical system of claim 1, wherein at least two of the plurality of processing circuits, and at least two of the plurality of timing circuits, are integrated into a single device; and wherein at least some of the plurality of processing circuits and at least some of the plurality of timing circuits are integrated into devices other than the single device.

13. The medical system of claim 1, wherein the plurality of processing circuits, the plurality of timing circuits, and the processor are dispersed across two or more devices connected via a network.

14. The medical system of claim 1, wherein a processing circuit of the plurality of processing circuits is configured to be dynamically connected to and disconnected from the processor, and wherein the processing circuit is configured to communicate with the processor only when the processing circuit is dynamically connected.

15. The medical system of claim 1, wherein the plurality of processing circuits include at least one treatment circuit configured to administer a treatment to a patient and the treatment circuit includes at least one of a ventilator and a defibrillator shock device.

16. The medical system of claim 1, wherein each timing circuit of at least some of the plurality of timing circuits is configured to:

receive a synchronization message having a time stamp from another timing circuit acting as a master timing circuit;

send a delay request message at a delay request sending time;

determine a master-slave time difference based on at least the time stamp and the delay request sending time; and adjust the clock of the timing circuit based on the master-slave time difference.

17. The medical system of claim 1, wherein each timing circuit is configured to:

determine whether to act as a master timing circuit or a slave timing circuit;

when acting as a slave timing circuit, to:

receive a synchronization message having a time stamp from another timing circuit acting as a master timing circuit, send a delay request message at a delay request sending time, determine a master-slave time difference based on at least the time stamp and the delay request sending time, and adjust the clock of the timing circuit based on the master-slave time difference, and when acting as a master timing circuit, to:

send the synchronization message having the time stamp, and receive the delay request message from another timing circuit acting as a slave timing circuit.

18. The medical system of claim 17, wherein at least some of the timing circuits are configured to determine whether to act as a master timing circuit or a slave timing circuit based on a pre-defined setting.

19. The medical system of claim 17, wherein each timing circuit of at least some of the timing circuits is configured to determine whether to act as a master timing circuit or a slave timing circuit based on communications with at least one other timing circuit.

20. The medical system of claim 17, wherein each of the plurality of timing circuits is further configured to:

when acting as a master timing circuit:

send a delay response message in response to the delay request message, and when acting as a slave timing circuit:

receive the delay response message at a delay response receipt time from the other timing circuit acting as the master timing circuit, and determine the master-slave time difference based on at least the delay response receipt time.

21. The medical system of claim 17, wherein the master timing circuit is further configured to send the at least one second time stamped signal and the slave timing circuit is further configured to receive the at least one second time stamped signal from the master timing circuit.

22. The medical system of claim 21, wherein the master timing circuit is further configured to save the time stamp of the synchronization message.

23. The medical system of claim 22, wherein the at least one second time stamped signal comprises at least the saved time stamp of the synchronization message.

24. The medical system of claim 21, wherein the master timing circuit is further configured to send the at least one second time stamped signal after sending the synchronization message.

25. The medical system of claim 24, wherein a time stamp of the sent at least one second time stamped signal is according to a local clock of the master timing circuit.

26. The medical system of claim 21, wherein the slave timing circuit is further configured to receive the at least one second time stamped signal from the master timing circuit before sending the delay request message.

27. The medical system of claim 1, wherein the plurality of processing circuits are configured to form a secure communications network and to dynamically join or leave the secure communications network.

28. The medical system of claim 1, wherein the medical system is configured to output an indication representative of the communication latency between timing circuits to a medium for user review.

29. The medical system of claim 1,
   wherein one of the plurality of timing circuits is configured to act as a master timing circuit and another of the plurality of timing circuits is configured to act as a slave timing circuit, and
   wherein the master timing circuit is configured to send the at least one second time stamped signal to the slave timing circuit.

30. The medical system of claim 29, wherein the at least one second time stamped signal comprises a sent time stamp according to a local clock of the master timing circuit.

31. The medical system of claim 29, wherein the at least one second time stamped signal comprises a received time stamp according to a local clock of the master timing circuit.

* * * * *

UNITED STATES PATENT AND TRADEMARK OFFICE
CERTIFICATE OF CORRECTION

PATENT NO. : 10,561,320 B2
APPLICATION NO. : 15/387119
DATED : February 18, 2020
INVENTOR(S) : Bruce Edwards et al.

Page 1 of 1

It is certified that error appears in the above-identified patent and that said Letters Patent is hereby corrected as shown below:

On the Title Page

Item (72) please correct the name of the second inventor from:
"Tim Stever" to --Timothy F. Stever--

Signed and Sealed this
Thirtieth Day of June, 2020

Andrei Iancu
*Director of the United States Patent and Trademark Office*